US012793819B2

(12) United States Patent
Awasthi

(10) Patent No.: US 12,793,819 B2
(45) Date of Patent: Nov. 10, 2026

(54) METHODS AND APPARATUSES FOR SYNTHESIZING TIME SERIES DATA AND DIAGNOSTIC DATA

(71) Applicant: Anumana, Inc., Cambridge, MA (US)

(72) Inventor: Samir Awasthi, Boston, MA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/395,399

(22) Filed: Dec. 22, 2023

(65) Prior Publication Data

US 2025/0210158 A1 Jun. 26, 2025

(51) Int. Cl.
*G16H 10/60* (2018.01)
*G06N 20/00* (2019.01)

(52) U.S. Cl.
CPC ............. *G16H 10/60* (2018.01); *G06N 20/00* (2019.01)

(58) Field of Classification Search
CPC ............................... G16H 10/60; G06N 20/00
See application file for complete search history.

(56) References Cited

U.S. PATENT DOCUMENTS

| | | | | |
|---|---|---|---|---|
| 8,948,854 | B2 | 2/2015 | Friedman et al. | |
| 11,103,194 | B2 | 8/2021 | Galloway et al. | |
| 11,445,918 | B2 | 9/2022 | Peterson | |
| 2014/0066799 | A1 | 3/2014 | Sherman | |
| 2018/0292978 | A1* | 10/2018 | Davies | G16H 15/00 |
| 2018/0350468 | A1* | 12/2018 | Friedman | A61B 5/14532 |
| 2020/0294665 | A1* | 9/2020 | Neumann | G06N 20/00 |
| 2020/0337648 | A1 | 10/2020 | Saripalli et al. | |
| 2020/0397313 | A1 | 12/2020 | Attia et al. | |
| 2021/0004714 | A1* | 1/2021 | Neumann | G06N 5/02 |

(Continued)

FOREIGN PATENT DOCUMENTS

| | | | | |
|---|---|---|---|---|
| WO | 2020086865 | A1 | 4/2020 | |
| WO | WO-2021050928 | A1 * | 3/2021 | G16H 50/20 |

(Continued)

OTHER PUBLICATIONS

Naz et al., From ECG signals to images: a transformation based approach for deep learning, (journal), Feb. 10, 2021, PeerJ Computer Science, 7: e386, National Library of Medicine.

(Continued)

*Primary Examiner* — Steven G.S. Sanghera
*Assistant Examiner* — Pierre L Maccagno
(74) *Attorney, Agent, or Firm* — CALDWELL LLC

(57) ABSTRACT

An apparatus for synthesizing time series data and diagnostic data is provided. The apparatus includes at least a processor and a memory communicatively connected to the at least a processor. The memory instructs the processor to receive time series data and generate at least one time series label as a function of the time series data, wherein generating at least one time series label as a function of the time series data includes generating a first time series label using a first label machine-learning model and generating a second time series label using a second label machine learning model. The memory also instructs the processor to determine at least one recommendation datum as a function the at least one time series label, generate a time series model comprising the time series input, and overlay the at least one recommendation datum onto the time series model.

18 Claims, 9 Drawing Sheets

(56) References Cited

U.S. PATENT DOCUMENTS

| | | | | |
|---|---|---|---|---|
| 2022/0000410 | A1* | 1/2022 | Baram | A61B 5/363 |
| 2022/0032075 | A1 | 2/2022 | Cascella | |
| 2022/0047201 | A1* | 2/2022 | Attia | A61B 5/361 |
| 2022/0293272 | A1* | 9/2022 | Pang | G16H 10/20 |
| 2023/0218238 | A1 | 7/2023 | Rattan et al. | |
| 2023/0380748 | A1* | 11/2023 | Engebretsen | A61B 5/352 |

FOREIGN PATENT DOCUMENTS

| | | | | |
|---|---|---|---|---|
| WO | WO-2022226642 | A1 * | 11/2022 | G06N 20/00 |
| WO | 2023/019022 | A1 | 2/2023 | |
| WO | 2023/060399 | A1 | 4/2023 | |
| WO | 2023/212297 | A1 | 11/2023 | |

OTHER PUBLICATIONS

European Search Report; EP24222546.4; Date: Apr. 3, 2025.

* cited by examiner

METHODS AND APPARATUSES FOR SYNTHESIZING TIME SERIES DATA AND DIAGNOSTIC DATA

FIELD OF THE INVENTION

The present invention generally relates to the field of artificial intelligence. In particular, the present invention is directed to methods and apparatuses for synthesizing time series data and diagnostic data.

BACKGROUND

Typically, time series data presents limited information associated with the care of patients. Time series data is difficult to understand. As such, it is difficult for patients and doctors to gain a complete understanding of what information they are looking at and why it is important.

SUMMARY OF THE DISCLOSURE

In an aspect, an apparatus for synthesizing time series data and diagnostic data is provided. The apparatus includes at least a processor and a memory communicatively connected to the at least a processor. The memory instructs the processor to receive time series data and generate at least one time series label as a function of the time series data, wherein generating at least one time series label as a function of the time series data comprises generating a first time series label using a first label machine-learning model and generating a second time series label using a second label machine learning model. The memory also instructs the processor to determine at least one recommendation datum as a function the at least one time series label, generate a time series model comprising the time series input, and overlay the at least one recommendation datum onto the time series model.

In another aspect, a method for synthesizing time series data and diagnostic data is provided. The method includes receiving, by at least a processor, time series data and generating, by the at least a processor, at least one time series label as a function of the time series data, wherein generating at least one time series label as a function of the time series data comprises generating a first time series label using a first label machine-learning model and generating a second time series label using a second label machine learning model. The method also includes determining, by the at least a processor, at least one recommendation datum as a function the at least one time series label, generating, by the at least a processor, a time series model comprising the time series input, and overlaying, by the at least a processor, the at least one recommendation datum onto the time series model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for synthesizing time series data and diagnostic data. In an embodiment, an apparatus for synthesizing time series data and diagnostic data is provided. The apparatus includes at least a processor and a memory communicatively connected to the at least a processor. The memory instructs the processor to receive time series data and generate at least one time series label as a function of the time series data. The memory also instructs the processor to determine at least one recommendation datum as a function the at least one time series label, generate a time series model comprising the time series input, and overlay the at least one recommendation datum onto the time series model. Exemplary embodiments illustrating aspects of the present disclosure are described below in the context of several specific examples.

Figure 1:
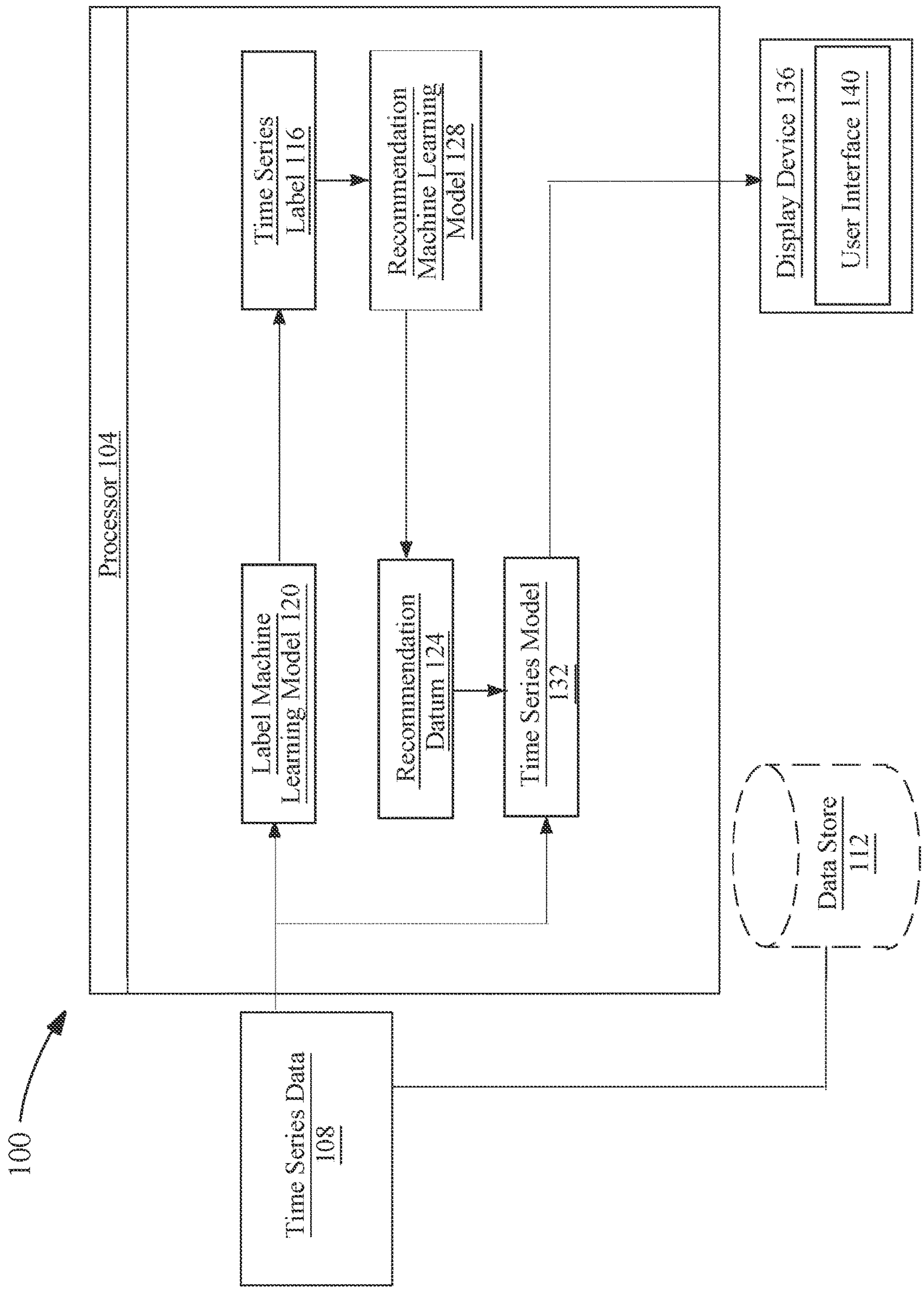
FIG. 1 is block diagram of an exemplary embodiment of an apparatus for synthesizing time series data and diagnostic data.

Referring now to FIG. 1, an exemplary embodiment of an apparatus 100 for synthesizing time series data and diagnostic data is illustrated. Apparatus 100 includes a processor 104. Processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory. Memory is communicatively connected to processor 104. Memory may contain instructions configuring processor 104 to perform tasks disclosed in this disclosure. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, apparatus, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, without limitation, via a bus or other facility for intercommunication between elements of a computing device. Communicative connecting may also include indirect connections via, for example, and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, processor 104 is configured to receive time series data 108. As used in the current disclosure, a "time series data" is a type of data that involves the sequential recording of observations or measurements at regular intervals over time. These observations can be related to various physiological, clinical, or health-related parameters, and they are essential for monitoring, diagnosing, and treating medical conditions. Time series data 108 may include data points that are collected at discrete time intervals, which can be seconds, minutes, hours, days, or even longer, depending on the specific context. This temporal aspect allows healthcare professionals to track changes in patients over time. Time series data 108 may encompass various types of data, such as vital signs (e.g., heart rate, blood pressure, temperature), electrocardiograms (ECG), electroencephalograms (EEG), lab test results, imaging data (e.g., MRI or CT scans), pulse oximetry, blood pressure and more. These diverse data sources provide a comprehensive view of a patient's health. Time series data 108 may be used in the diagnostic process to detect anomalies, patterns, or trends that indicate the presence of a medical condition. For example, an abnormal ECG pattern might suggest cardiac arrhythmia. Time series data 108 may include information from a plurality of electronic health records (EHRs). As used in the current disclosure, "electronic health records" are digital records containing a patient's medical history, diagnoses, medications, treatment plans, and other relevant information. EHRs are used by healthcare providers to track and manage patient care. Time series data 108 may include information from a plurality of medical imaging data. As used in the current disclosure, "medical imaging data" refers to the visual representations of the internal structures and functions of the human body obtained through various imaging techniques. Medical imaging data may include data associated with X-rays, CT scans, magnetic resonance imaging, ultrasounds, PET scans, nuclear medicine imaging, mammography, fluoroscopy, and the like. Additionally, or alternatively, processor 104 may be configured to retrieve patient data for a patient associated with time series data 108 from electronic health records. As used in this disclosure, "patient data" is any data associated with a patient. For example, patient data may include name, age, birthday, and the like.

With continued reference to FIG. 1, time series data 108 may include a plurality of electrocardiogram (ECG) signals from a patient. As used in the current disclosure, a "electrocardiogram signal" is a signal representative of electrical activity of heart. The ECG signal may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves provide information about the duration and regularity of various phases of the cardiac cycle. The ECG signal can help diagnose various heart conditions, such as arrhythmias, myocardial infarction (heart attack), conduction abnormalities, and electrolyte imbalances. In an embodiment, each sensor 116 may generate an individual ECG signal.

With continued reference to FIG. 1, the plurality of electrocardiogram signals may capture a temporal view of cardiac electrical activities. A "temporal view," as used in the current disclosure, refers to the analysis and visualization of heart-related events and activity over time. A temporal view may include patterns, changes, and dynamics of cardiac activity over time. A temporal view may include information surrounding the rhythm of the heart, including the regularity or irregularity of heartbeats. It allows for the identification of various rhythm abnormalities such as tachycardia (e.g., fast heart rate), bradycardia (e.g., slow heart rate), or arrhythmias (e.g., irregular heart rhythms). A temporal view of cardiac activities in three dimensions may refer to a visualization that represents the temporal evolution of cardiac events or phenomena in a three-dimensional space. It provides a comprehensive understanding of how various cardiac activities change over time. The ECG signal may move through the 3D space of the heart over time. The signal does not just move forward in time, it also moves through the physical space of the heart, from SA node through atria, to AV node, and then through the ventricles. Such movement of the electrical signal through the heart's physical space over time can be referred to as "spatiotemporal excitation and propagation" which could be captured by plurality of ECG signals. It is a way of observing and analyzing the timing and sequence of the heart's electrical activity as it moves through the physical structure of the heart. In the current case the dimensions may include axis representing time, spatial dimensions, and cardiac activity. By combining the temporal, spatial, and cardiac activity dimensions, the temporal view of cardiac activities in three dimensions allows for a comprehensive visualization and analysis of dynamic changes occurring within the heart. It can be used to study phenomena like electrical conduction, ventricular wall motion, valve function, blood flow dynamics, or the interaction between different regions of the heart. This visualization approach provides valuable insights into the complex temporal dynamics of cardiac activities and aids in understanding cardiac function, pathology, and treatment evaluation.

With continued reference to FIG. 1, the plurality of electrocardiogram signals may be generated using at least one sensor 116. As used in this disclosure, a "sensor" is a device that is configured to detect an input and/or a phenomenon and transmit information related to the detection. Sensor 116 may detect a plurality of data. A plurality of data detected by at least one sensor 116 may include, but is not limited to, electrocardiogram signals, heart rate, blood pressure, electrical signals related to the heart, and the like. In one or more embodiments, and without limitation, at least one sensor 116 may include a plurality of sensors. In one or more embodiments, and without limitation, at least one sensor 116 may include one or more electrodes, and the like. Each electrode of one or more electrodes used for an ECG may be small sensors or conductive patches that are placed on specific locations on the body to detect and record the electrical signals generated by a subject heart. At least one sensor 116 may be configured to serve as an interface between the body and the ECG machine, allowing for the measurement and recording of the heart's electrical activity. At least one sensor 116 may include 10 electrodes used for a standard 12-lead ECG, placed in specific positions on the chest and limbs of the patient. These electrodes are typically made of a conductive material, such as metal or carbon, and are connected to lead wires that transmit the electrical signals to the ECG machine for recording.

With continued reference to FIG. 1, at least one sensor 116 may be placed on each limb, wherein there may be a sensor at least one sensor 116 on each arm and leg. These sensors may be labeled I, II, III, V1, V2, V3, V4, V5, V6, and the like. For example, Sensor I may be placed on the left arm, Sensor II may be placed on the right arm, and Sensor III may be placed on the left leg. Additionally, a plurality of sensors of at least one sensor 116 may be placed on various portions of the patient's torso and chest. For example, a sensor V1 may be placed in the fourth intercostal space at both the right sternal borders and sensor V2 may be fourth intercostal space at both the left sternal borders. A sensor V3 may also be placed between sensors V2 and V4, halfway between their positions. Sensor V4 may be placed in the fifth intercostal space at the midclavicular line. Sensor V5 may be placed horizontally at the same level as sensor V4 but in the anterior axillary line. Sensor V6 may be placed horizontally at the same level as V4 and V5 but in the midaxillary line.

With continued reference to FIG. 1, at least one sensor 116 may include augmented unipolar sensors. These sensors may be labeled as aVR, aVL, and aVF. These sensors may be derived from the limb sensors and provide additional information about the heart's electrical activity. These leads are calculated using specific combinations of the limb leads and help assess the electrical vectors in different orientations. For example, aVR may be derived from Sensor II and Sensor III. In another example, aVL may be derived from sensor I and Sensor III. Additionally, aVF may be derived from Lead I and Lead II. The combination of limb sensors, precordial sensors, and augmented unipolar sensors allows for a comprehensive assessment of the heart's electrical activity in three dimensions. These leads capture the electrical signals from different orientations, which are then transformed into transformed coordinates to generate vectorcardiogram (VCG) representing magnitude and direction of electrical vectors during cardiac depolarization and repolarization. Transformed coordinates may include one or more a Cartesian coordinate system (x, y, z), polar coordinate system (r, θ), cylindrical coordinate system (ρ, φ, z), or spherical coordinate system (r, θ, φ). In some cases, transformed coordinates may include an angle, such as with polar coordinates, cylindrical coordinates, and spherical coordinates. In some cases, VCG may be normalized thus permitting full representation with only angles, i.e., angle traversals. In some cases, angle traversals may be advantageously processed with one or more processes, such as those described below and/or spectral analysis.

With further reference to FIG. 1, in an embodiment, time series data 108 may comprise at least one static image. This static image may be sourced from at least one sensor 116, described above, which may include any sensor capable of collecting time series data including without limitation a 12-lead ECG machine such as a Biocare 12-lead ECG machine, a 6-lead ECG machine, an exercise ECG machine, a Holter monitor, a wearable device such as an exercise ECG tracker, a smart watch having a wrist sensor, or the like, and/or any other device capable of capturing ECG data and/or any component thereof. At least one sensor 116 may alternatively or additionally include any type of device capable of capturing electroencephalograms (EEGs), magnetic resonance imagers, electromyography scans (EMGs), galvanic skin response sensors, fitness trackers, blood pressure monitors, sleep trackers, blood-oxygen level monitors, heart rate trackers, diabetes or herpes trackers, immune disorder logs, or any other medical imaging or time series data capable of being plotted. At least one sensor 116 may refer to standalone devices, such as those used exclusively in established medical facilities, such as magnetic resonance imagers, computerized tomography scans, x-rays, ultrasounds, radiotherapy equipment, intravenous monitors, or any other standalone device. While this disclosure openly discusses medical devices, the disclosure applies to any time series collection devices including non-medical applications wherein the exportable information is limited to static images of the time series data. Additionally, at least one sensor 116 may be a plurality of handheld, or wearable devices such as a Fitbit watch or wristband or other wearable heart rate monitor, a pacemaker or other cardiac rhythm management implant, glucose monitor, smart watch, real-time blood pressure sensors, temperature monitors, respiratory rate monitors or other biosensors, or any other wearable monitor.

Still referring to FIG. 1, for the purposes of this disclosure, “static image time series of measured values” is a digital or printed image compiling information usually derived from a digital device interrogation output, formatted based on the source device protocols and containing time series data capable of being plotted on a two-dimensional axis. Static time series image may be in image format, wherein the discrete data points may be identified and interpreted from the image. In other applications of Generative Adversarial Networks, inputs may include a plurality of different types or domains, including without limitation text, code, images, molecules, audio (e.g., music), video, and robot actions (e.g., electromechanical system actions). As a non-limiting example, an ECG recording’s data set of voltage measured over a 30-second period at a frequency ranging from 50 Hz-500 Hz may be plotted, recorded, and saved or printed for use by processor 104 as static time series image. Time-plotted voltages, especially within the range of voltages expected to be detected from a human heart through skin contact, exported from any capable device, may be used for static time series image 108. In a non-limiting embodiment, static time series image may further include any set of plotted time series data which may be valuable within a separate set of domain protocols other than its original static image source.

Further referring to FIG. 1, as a non-limiting example, static time series image may include a patient’s blood pressure plotted over a specified time, heart rate, blood-sugar, stress test data, or any relevant time series data associated with a patient. Static time series image may additionally contain identifying or descriptive data meant primarily to support time series data 108. For example, static time series image may include timing information for when the time series was initially recorded, location data, or any other appropriate information. These additional data tags embedded within the static time series image may be used as training data to support pairing input data to output data. Specifically, in a non-limiting embodiment, in the example of an ECG time series, various inputs and grouping mechanisms may aid diagnosis of a cardiac irregularity, which may be an indicator of an atrial or ventricular fibrillation. Once confirmed by a medical professional, especially if in multiple instances of repeating similar circumstances, the machine learning model may identify patterns across these instances such that it could grow to act as an early warning system for more severe conditions. Continuing in this non-limiting embodiment, various types of input data included in static time series image may be grouped together in a logical manner to support these types of early warning diagnosis support. In an additional non-limiting embodiment, heart rate training data may support detecting and diagnosing a tachycardia or bradycardia condition, each of which may be indicative of severe or complex issues needing immediate response care. Additionally, blood pressure, electromyography data, computerized tomography (CT) scans, magnetic resonance imaging (MRI), or any other device where data is collected over time and is operative only within an initial domain protocol may be included in static time series image.

Still referring to FIG. 1, static time series image may consist of various ECG formats. In a non-limiting embodiment, a 12-lead ECG may use various recording formats including 3×4, 3×4+R, 3×4+3R, 6×2, 6×2+R, 6×2+3R, 12, 12+R, 12+3R, and/or rhythm mode, then may store the data so recorded within its proprietary system; such a device may enable exporting the collected data to a JPEG, PNG, TIFF, Bitmap, GIF, EPS, RAW image file, or other form of digital image. Additionally, any type of image of time series data may be screenshot and/or printed and subsequently used as input for static time series image. As a further non-limiting example, an ECG machine may use application of Minnesota Code, CSE and/or AHA database formatting guidelines, as well as support for an ECG management system or HL7 protocol. Each of these specified formats and data exchange protocols may be interoperable with other ECG devices, but they may be exclusive to a hardware sensor and/or sensor component relied upon to generate the data.

Still referring to FIG. 1, static time series image may include multiple time series each with separate domain protocol formats. Specifically, processor 104 may receive static time series image that may include a first time series and a second time series; each of first time series and second time series may include time-series data pertaining to the same category of process being measured, such as time-series data from the same type of diagnostic process or the like. In an embodiment, first time series may be recorded by and/or received from a first device while second time series may be recorded by and/or received from a second device; first device and second device may be different devices and/or different types of devices and may record using the same initial domain protocol as each other or may record in two distinct initial domain protocols. Initial time series data may include a plurality of sets of time series data from a plurality of devices, of which any two devices may include a first device and second device as described above; such initial time series data may include datasets in a plurality of distinct initial domain protocols. As a non-limiting example, multiple ECG data sets, which may be recorded with multiple initial domain protocols, may be used as static time series image to develop a single common protocol for the data sets from each ECG as described in further detail below. Conversion of initial domain protocols to a common protocol may enable a medical professional to use any or all such datasets within either or both hardware configurations to analyze the ECG data. Development of a common domain protocol may be used to support future conversions.

With continued reference to FIG. 1, time series data 108 may be received through a network of connected devices. In a non-limiting embodiment, a device that captures one or more elements of time series data and/or performs one or more steps described in this disclosure may be communicatively connected to one or more other devices, including without limitation any devices described in this disclosure, a local area network (LAN), a wide area network (WAN) such as the Internet or a subset thereof, such that all recorded data may be accessible via any other web enabled device. In this way, time series data 108 may be requested and imported into processor 104 via web or local network interface. Processor and/or another device may divide processing tasks between multiple processors to accelerate delivery of completed time series data 108.

With continued reference to FIG. 1, time series data 108 may be received through a direct file importing process, wherein static time series image 108 may be saved and downloaded to processor 104. This may include file transfers from any type of hard drive or other memory type exchange or replication. Static time series image 108 may be locally generated in cases where processor 104 is built in conjunction with or contained within an ECG-capable device. Static time series image 108 may also be imported into processor 104 through manual generation, wherein a user populates all necessary data by any mechanism wherein the minimum required set of time series data is made available to apparatus 100.

With continued reference to FIG. 1, time series data 108 may be received from a scanning device. In cases where the time series data is only available in a tangible, paper format, the image may be scanned in using any scanner with sufficient clarity in its scanning process. Processor 104 may allow for direct ingestion of the scanned time series image or may support a conversion to a preferred image format. Scanning of the time series image may be accomplished in any manner capable of generating a digital representation of the time series image to include mobile phone image scans, drum scanner scans, flatbed scans, or others.

Still referring to FIG. 1, processor 104 may rely on optical character recognition or optical character reader (OCR), executed by processor 104 to automatically convert images of written (e.g., typed, handwritten or printed) text into machine-encoded text. In some cases, recognition of at least a keyword from an image component may include one or more processes, including without limitation optical character recognition, optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases, a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning processes like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIG. 2 below. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool includes OCRopus. OCRopus development is led by German Research Centre for Artificial Intelligence in Kaiserslautern, Germany. In some cases, OCR software may employ neural networks, for example neural networks as taught in reference to FIGS. 5-6 below.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make use of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

Still referring to FIG. 1, image recognition and processing may build upon the character recognition methods discussed above. Time series data is generally less complex to interpret than the infinite possible image types, so a predefined analysis which targets time series types of data may be efficiently translated to an interrogable format, such that the image data may have numerical statistics applied and an underlying algorithm to define the time series graph. Translation of the raw image into the numerically defined time series format may rely on first the optical character recognition described above to interpret the axes and labels of the data. With the axes and labels defined, the time series numerical characteristics may be applied based on the timing and relative locations of peaks and troughs, consistency of the waveform, amplitudes, and any other identifiable features.

With continued reference to FIG. 1, processor 104 may be configured to receive time series data 108 from a data store 112. Data store 112 may be configured to store any data described herein. Processor 104 may be communicatively connected with data store 112. In some cases, data store 112 may be local to processor 104. Alternatively, data store 112 may be remote to processor 104 and communicative with processor 104 by way of one or more networks (e.g., a cloud network, a mesh network, or the like). In a non-limiting example, apparatus 100 may include a "cloud-based" system (i.e., a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connects directly, dynamically, and non-hierarchically to as many other computing devices as possible. A "network topology" as used in this disclosure is an arrangement of elements of a communication network.

Still referring to FIG. 1, in some cases, data store 112 may be implemented, without limitation, as a relational database, a key-value retrieval database such as a NOSQL database, or any other format or structure for use as a database that a person skilled in the art would recognize as suitable upon review of the entirety of this disclosure. Data store 112 may alternatively or additionally be implemented using a distributed data storage protocol and/or data structure, such as a distributed hash table or the like. Data store 112 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a data store or database may store, retrieve, organize, and/or reflect data and/or records as used herein, as well as categories and/or populations of data consistently with this disclosure.

In a non-limiting example, and still referring to FIG. 1, data store 112 may be an electronic health record system. As used in this disclosure, "electronic health record system" is a comprehensive and real-time collection of patient health information. In some cases, time series data 108 may be obtained using an application programing interface (API) of electronic health record system.

With continued reference to FIG. 1, processor 104 may be configured to receive time series data 108 using an application programming interface (API). As used herein, an "application programming interface" is a set of functions that allow applications to access data and interact with external software components, operating systems, or microdevices, such as another web application or computing device. An API may define the methods and data formats that applications can use to request and exchange information. APIs enable seamless integration and functionality between different systems, applications, or platforms. An API may deliver time series data 108 to apparatus 100 from a system/application that is associated with a user, medical provider, or other third party custodian of user information. An API may be configured to query for web applications or other websites to retrieve time series data 108. An API may be further configured to filter through web applications according to a filter criterion. In this disclosure, "filter criterion" are conditions the web applications must fulfill in order to qualify for API. Web applications may be filtered based off these filter criterion. Filter criterion may include, without limitation, web application dates, web application traffic, web application types, web applications addresses, and the like. Once an API filters through web applications according to a filter criterion, it may select a web application. Processor 104 may transmit, through the API, time series data 108 to apparatus 100. API may further automatically fill out user entry fields of the web application with the user credentials in order to gain access to the time series data 108. Web applications may include, without limitation, a medical database, hospital website, file scanning, email programs, third party websites, governmental websites, or the like.

With further reference to FIG. 1, processor 104 is configured to generate at least one time series label 116 as a function of the time series data 108. As used in the current disclosure, a "time series label" is a mark for a portion of time series data that may be of interest for review by a medical professional. These time series labels 116 and associated time series data may be used to evaluate health, diagnose diseases, monitor wellness, or understand the functioning of the body for a patient. Further, time series labels 116 and associated time series data may indicate a potential issue with health of a person associated with time series data 108.

Further referring to FIG. 1, processor 104 may generate at least one time series label 116 in real-time with time series data 108. As used in the current disclosure, a "real-time" refers to the immediate or instantaneous processing, analysis, or display of data as it occurs or becomes available, without any noticeable delay involves the continuous collection, processing, and interpretation of data. Generating at least one time series label 116 may involve a continuous collection, processing, and interpretation time series data 108 by processor 104. Processor 104 may be configured to extract a plurality of features from the time series data 108 in real-time to generate at least one time series label 116. Feature extraction is a process that may include identifying and quantifying relevant characteristics in the time series data 108. These features can be statistical, spectral, or time-domain measures that capture specific aspects of time series data 108.

Referring further to FIG. 1, additionally, or alternatively, processor 104 may generate at least one time series label 116 using a label machine-learning model 120. As used in the current disclosure, a "label machine-learning model" is a machine-learning model that is configured to generate time series labels 116 for time series data. Label machine-learning model 120 may be consistent with any machine-learning model described herein and below in FIG. 2. Inputs to the label machine-learning model 120 may include time series data 108, ECG data, and the like. Outputs from the label machine-learning model 120 may include time series labels 116 tailored to the time series data 108. Label training data may include a plurality of data entries containing a plurality of inputs that are correlated to a plurality of outputs for training a processor by a machine-learning process. In an embodiment, label training data may include a plurality of time series data as inputs correlated to examples of time series labels as outputs. Label training data may be received from database. In an embodiment, plurality of time series data and time series labels for label training data and label training data may be anonymized data. As used in this disclosure, "anonymized data" is time series data and time series label data that has been modified or disguised in a way that makes it impossible or impractical to identify the user associated with the time series data and/or time series label data, while still retaining its usability for training label machine-learning model. In one exemplary embodiment, metadata for time series data and time series label data may be removed from time series data and time series label. Removing metadata may include separating metadata from time series data and time series label and discarding such metadata. Additionally, or alternatively, metadata may be altered withing time series data and time series label data. Altering metadata, may include restructuring the metadata such that identifying user associated with metadata may be impossible and/or impractical. As used in this disclose, "metadata" refers to descriptive or informational data that provides details about a user associated time series data and/or time series label data. In an embodiment, label training data may be iteratively updated as a function of the input and output results of past iterations of label machine-learning model 120 or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

Continuing to refer to FIG. 1, in a non-limiting example, label machine-learning model 120 may comprise a plurality of machine learning models. Label machine-learning model 120 may comprise a first label machine-learning model and a second label machine learning model, wherein the first label machine-learning model and the second label machine learning model are configured to determine different labels for time series data. As a non-limiting example first label machine-learning model may determine labels relating to cardiac ejection-fraction. In some embodiments, first label machine-learning model may generate a first time series label, whereas second label machine-learning model may generate a second time series label. As a non-limiting example first label machine-learning model may determine labels relating to atrial fibrillation. In an embodiment, a machine learning model for label machine-learning model 120 described herein may be consistent with any ejection-fraction prediction model disclosed in U.S. patent application Ser. No. 16/754,007, filed on Apr. 6, 2020, entitled "ECG-BASED CARDIAC EJECTION-FRACTION SCREENING", the entirety of which is incorporated herein by reference. In a further non-limiting example, additionally, or alternatively, a machine learning model for label machine-learning model 120 described herein may be consistent with any neural network disclosed in U.S. patent application Ser. No. 17/275,276, filed on Mar. 11, 2021, entitled "NEURAL NETWORKS FOR ATRIAL FIBRILLATION SCREENING", the entirety of which is incorporated herein by reference. In another non-limiting example, additionally, or alternatively, a machine learning model for label machine-learning model 120 described herein may be consistent with any learning system disclosed in U.S. patent application Ser. No. 18/151,673, filed on Jan. 9, 2023, entitled "NONINVASIVE METHODS FOR QUANTIFYING AND MONITORING LIVER DISEASE SEVERITY", the entirety of which is incorporated herein by reference. Additionally, or alternatively, a machine learning model for label machine-learning model 120 described herein may be consistent with any learning system disclosed in International Pat. App. Ser. No. PCT/US2023020362, filed on Apr. 28, 2023, entitled "ARTIFICIAL INTELLIGENCE ENHANCED SCREENING FOR CARDIAC AMYLOIDOSIS BY ELECTROCARDIOGRAMY", the entirety of which is incorporated herein by reference. Additionally, or alternatively, a machine learning model for label machine-learning model 120 described herein may be consistent with any learning system disclosed in International Pat. App. Ser. No. PCT/US2022040362, filed on Aug. 30, 2023, entitled "MACHINE-LEARNING FOR PROCESSING LEAD-INVARIANT ELECTROCARDIGRAM INPUTS", the entirety of which is incorporated herein by reference. Additionally, or alternatively, a machine learning model for label machine-learning model 120 described herein may be consistent with any system and method disclosed in U.S. patent application Ser. No. 13/810,064, filed on Mar. 29, 2013, entitled "NON-INVASIVE MONITORING OF PHYSIOLOGICAL CONDITIONS", the entirety of which is incorporated herein by reference. Additionally, or alternatively, a machine learning model for label machine-learning model 120 described herein may be consistent with any machine learning model disclosed in U.S. patent application Ser. No. 15/778,405, filed on May 23, 2018, entitled "PROCESSING PHYSIOLOGICAL ELECTRICAL DATA FOR ANALYTE ASSESSMENTS", the entirety of which is incorporated herein by reference. Additionally, or alternatively, a machine learning model for label machine-learning model 120 described herein may be consistent with any machine learning model disclosed in U.S. patent application Ser. No. 15/842,419, filed on Dec. 14, 2017, entitled "SYSTEMS AND METHODS OF ANALYTE MEASUREMENT ANALYSIS", the entirety of which is incorporated herein by reference. Additionally, or alternatively, a machine learning model for label machine-learning model 120 described herein may be consistent with any generative model disclosed in U.S. patent application Ser. No. 18/517,640, filed on Nov. 22, 2023, entitled "SYSTEM AND APPARATUS FOR GENERATING IMAGING INFORMATION BASED ON AT LEAST A SIGNAL", the entirety of which is incorporated herein by reference. In an embodiment, label machine-learning model 120 may be any combination of machine-learning models described herein. In such an embodiment, time series label 116 may include an output from each machine learning model of plurality of machine learning model for label machine learning model 120.

With further reference to FIG. 1, in some cases, label machine-learning model 120 and/or any machine learning model described herein may be executed remote to processor 104 and outputs may be communicated to processor 104 by way of one or more networks. For example, label machine-learning model 120 may be executed on a remote server and/or a remote device. Processor 104 may be configured to receive outputs of the label machine-learning model from remote device and/or remote server. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which processor 104 connects directly, dynamically, and non-hierarchically to as many other computing devices as possible. A "network topology" as used in this disclosure is an arrangement of elements of a communication network.

With continued reference to FIG. 1, additionally, or alternatively, processor 104 may be configured to identify relevant data from time series data 108 for time series labels 116. As used in this disclosure, "relevant data" is a portion of time series data that may be of interest for review by a medical professional. The relevant data may be reviewed and used by a medical professional to evaluate health, diagnose diseases, monitor wellness, or understand the functioning of the body for a patient. Further, relevant data may indicate a potential issue with health of a person and/or patient associated with time series data 108. In an embodiment, label machine-learning model 120 and/or any other machine learning model described herein may be configured to identify relevant data from time series data 108 for time series labels 116. Inputs to the label machine-learning model 120 may include time series data 108, ECG data, and the like. Outputs from the label machine-learning model 120 may include identified relevant data from the time series data 108. Label training data may include a plurality of data entries containing a plurality of inputs that are correlated to a plurality of outputs for training a processor by a machine-learning process. In an embodiment, label training data may include a plurality of time series data as inputs correlated to examples of relevant data as outputs.

Still referring to FIG. 1, processor 104 may be configured to generate a machine-learning model, such as label machine-learning model, using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P (A/B)=P (B/A) P (A)=P (B), where P (A/B) is the probability of hypothesis A given data B also known as posterior probability; P (B/A) is the probability of data B given that the hypothesis A was true; P (A) is the probability of hypothesis A being true regardless of data also known as prior probability of A; and P (B) is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

Still referring to FIG. 1, processor 104 may be configured to generate a machine-learning model, such as diagnostic machine-learning model, using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm $$l = \sqrt{\sum_{i=0}^{n} a_i^2},$$

where $a_i$ is attribute number experience of the vector. Scaling and/or normalization may function to make vector comparison independent of absolute quantities of attributes, while preserving any dependency on the similarity of attributes; this may, for instance, be advantageous where cases represented in training data are represented by different quantities of samples, which may result in proportionally equivalent vectors with divergent values.

With continued reference to FIG. 1, processor 104 may generate a confidence score as a function of generating the at least one time series label 116. As used in the current disclosure, a "label confidence score" is quantitative measurement of the accuracy of the generation of the at least one time series label 116. Accuracy of generation of the at least one time series label 116 may refer to likelihood of an accurate diagnosis of the condition, disease, or issue experienced by the patient. A processor 104 may generate a confidence score for each time series label 116 assigned to the time series data. Processor 104 may calculate a label confidence score based on the similarity or dissimilarity between the two time series label 116 based on the diagnostic features that have been extracted from time series data 108. Various similarity metrics can be employed, such as Euclidean distance, cosine similarity, Jaccard similarity, or any other appropriate measure for the type of data being compared. Processor 104 may use the calculated similarity or dissimilarity values to generate a confidence score. This score may represent the level of confidence or certainty in the accuracy in the generated time series label 116. The score can be computed based on statistical methods, probability models, or decision rules based on the time series data and the extracted diagnostic features. A label confidence score may be used to normalize one or more time series labels 116 onto a comparable scale. Normalization techniques can include min-max scaling, z-score normalization, or logarithmic transformation. In an embodiment, if the time series label 116 is likely to be accurate then the label confidence score may be high, conversely time series label 116 is likely inaccurate then the label confidence score may be low. Label confidence score may be expressed as a numerical score, a linguistic value, alphanumeric score, or an alphabetical score. Label confidence score may be represented as a score used to reflect the level of accuracy of the time series label. A non-limiting example, of a numerical score, may include a scale from 1-10, 1-100, 1-1000, and the like, wherein a rating of 1 may represent an inaccurate time series label, whereas a rating of 10 may represent an accurate time series label. In another non-limiting example, linguistic values may include, "Highly Accurate," "Moderately Accurate," "Moderately Inaccurate," "Highly Inaccurate," and the like. In some embodiments, linguistic values may correspond to a numerical score range. For example, time series label that receives a score between 50-75, on a scale from 1-100, may be considered "Moderately Accurate."

With continuing reference to FIG. 1, processor 104 may be configured to determine at least one recommendation datum 124 as a function the at least one time series label 116. As used in the current disclosure, "recommendation datum" is data associated with recommendation associated with a potential user medical condition or health issue. Processor 104 may generate recommendation datum 124 as a function of the time series data 108 and at least one time series label 116. In an exemplary embodiment, recommendation datum 124 may be a recommended action used to diagnose and/or confirm a suspected condition or a suspected disease a patient is suspected to be suffering from based on the at least one time series label 116 and time series data associated therewith. In some embodiments, at least one recommendation datum 124 may include a first recommendation datum and a second recommendation datum. In some embodiments, first recommendation datum may be related to first time series label and second recommendation datum may be related to second time series label. In some embodiments, first recommendation datum may be generated using first time series label. In some embodiments, first recommendation datum may be generated using second time series label. For example, recommendation datum 124 may include a recommendation to follow up with a stress test, an echocardiogram, and the like. Additionally, recommendation datum 124 may include a recommendation to adjust a patient's diet to improve a patient's health. For example, recommendation datum 124 may include a recommendation to adjust a patient's diet to reduce saturated and trans fats, increase intake of healthy fats, increase intake of lean proteins, and the like. Further, recommendation datum 124 may include a change to physical activity. For example, recommendation datum 124 may include a recommendation to increase a user's physical activity to at least 150 minutes of moderate-intensity aerobic activity or 75 minutes of vigorous-intensity aerobic activity per week, and the like.

Still referring to FIG. 1, processor 104 may be configured to generate at least one recommendation datum 124 using a recommendation machine-learning model 128. As used in the current disclosure, a "recommendation machine-learning model" is a machine-learning model that is configured to generate recommendation data based on time series data 108 and/or associated time series labels 116. Recommendation machine-learning model 128 may be consistent with any machine-learning model described herein and below in FIG. 2. Inputs to recommendation machine-learning model 128 may include time series data 108, ECG data, time series label data, and the like. Outputs from recommendation machine-learning model may include recommendation data tailored to the time series data 108 and/or time series labels 116. Recommendation training data may include a plurality of data entries containing a plurality of inputs that are correlated to a plurality of outputs for training a processor by a machine-learning process. In an embodiment, recommendation training data may include a plurality of time series data and time series labels as inputs correlated to examples of recommendation data as outputs. Recommendation training data may be received from database. In an embodiment, affliction training data may be iteratively updated as a function of the input and output results of past iterations of recommendation machine-learning model 128 or any other machine-learning model mentioned throughout this disclosure. Recommendation machine-learning model 128 may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

Continuing to refer to FIG. 1, in a non-limiting example, recommendation machine-learning model 128 may comprise a plurality of machine learning models. In an embodiment, a machine learning model for recommendation machine-learning model 128 described herein may be consistent with any recommendation model in U.S. patent application Ser. No. 16/754,007, filed on Apr. 6, 2020, entitled "ECG-BASED CARDIAC EJECTION-FRACTION SCREENING", the entirety of which is incorporated herein by reference. In a further non-limiting example, additionally, or alternatively, a machine learning model for recommendation machine-learning model 128 described herein may be consistent with any recommendation model disclosed in U.S. patent application Ser. No. 17/275,276, filed on Mar. 11, 2021, entitled "NEURAL NETWORKS FOR ATRIAL FIBRILLATION SCREENING", the entirety of which is incorporated herein by reference. In another non-limiting example, additionally, or alternatively, a machine learning model for recommendation machine-learning model 128 described herein may be consistent with any recommendation model disclosed in U.S. patent application Ser. No. 18/151,673, filed on Jan. 9, 2023, entitled "NONINVASIVE METHODS FOR QUANTIFYING AND MONITORING LIVER DISEASE SEVERITY", the entirety of which is incorporated herein by reference. Additionally, or alternatively, a machine learning model for recommendation machine-learning model 128 described herein may be consistent with any recommendation model disclosed in International Pat. App. Ser. No. PCT/US2023020362, filed on Apr. 28, 2023, entitled "ARTIFICIAL INTELLIGENCE ENHANCED SCREENING FOR CARDIAC AMYLOIDOSIS BY ELECTROCARDIOGRAMY", the entirety of which is incorporated herein by reference. Additionally, or alternatively, a machine learning model for recommendation machine-learning model 128 described herein m may be consistent with any recommendation model disclosed in International Pat. App. Ser. No. PCT/US2022040362, filed on Aug. 30, 2023, entitled "MACHINE-LEARNING FOR PROCESSING LEAD-INVARIANT ELECTROCARDIGRAM INPUTS", the entirety of which is incorporated herein by reference. Additionally, or alternatively, a machine learning model for recommendation machine-learning model 128 described herein may may be consistent with any recommendation model disclosed in U.S. patent application Ser. No. 13/810,064, filed on Mar. 29, 2013, entitled "NON-INVASIVE MONITORING OF PHYSIOLOGICAL CONDITIONS", the entirety of which is incorporated herein by reference. Additionally, or alternatively, a machine learning model for recommendation machine-learning model 128 described herein may be consistent with any recommendation model disclosed in U.S. patent application Ser. No. 15/778,405, filed on May 23, 2018, entitled "PROCESSING PHYSIOLOGICAL ELECTRICAL DATA FOR ANALYTE ASSESSMENTS", the entirety of which is incorporated herein by reference. Additionally, or alternatively, a machine learning model for recommendation machine-learning model 128 described herein may be consistent with any recommendation model disclosed in U.S. patent application Ser. No. 15/842,419, filed on Dec. 14, 2017, entitled "SYSTEMS AND METHODS OF ANALYTE MEASUREMENT ANALYSIS", the entirety of which is incorporated herein by reference. Additionally, or alternatively, a machine learning model for recommendation machine-learning model 128 described herein may be consistent with any recommendation model disclosed in U.S. patent application Ser. No. 18/517,640, filed on Nov. 22, 2023, entitled "SYSTEM AND APPARATUS FOR GENERATING IMAGING INFORMATION BASED ON AT LEAST A SIGNAL", the entirety of which is incorporated herein by reference.

With further reference to FIG. 1, in an embodiment, recommendation datum may comprise affliction data. As used in this disclosure, "affliction data" is data that identifies the condition of or name of the disease the user is suffering from based on known conditions/symptoms of the user. In a non-limiting example, abnormalities within time series data 108 and/or associated time series labels 116 may indicate the presence of abnormal rhythms (arrhythmias), such as atrial fibrillation or ventricular tachycardia. Relevant data may be extracted from time series data 108 and/or associated time series labels 116, such as peaks, trends, or statistical metrics. These features can help in characterizing the affliction data. In an embodiment, algorithms and machine learning techniques can be applied to recognize patterns and anomalies within the data. For instance, identifying irregular heart rhythms and the like. Processor 104 may be configured to compare the collected time series data 108 and/or associated time series labels 116 to reference data or established norms to assess whether time series data 108 and/or associated time series labels 116 fall within expected ranges. Processors 104 may use specialized diagnostic algorithms, which consider multiple parameters and historical data to make informed assessments. These algorithms can be based on clinical guidelines or specific domain knowledge.

Continuing to refer to FIG. 1, processor 104 may be configured to generate at least one affliction datum using an affliction machine-learning model. As used in the current disclosure, an "affliction machine-learning model" is a machine-learning model that is configured to generate affliction data based time series data 108 and/or associated time series labels 116. Affliction machine-learning model may be consistent with any machine-learning model described herein and below in FIG. 2. Inputs to the affliction machine-learning model may include time series data 108, ECG data, time series label data, and the like. Outputs from the affliction machine-learning model may include affliction data tailored to the time series data 108 and/or time series labels 116. Affliction training data may include a plurality of data entries containing a plurality of inputs that are correlated to a plurality of outputs for training a processor by a machine-learning process. In an embodiment, affliction training data may include a plurality of time series data and time series labels as inputs correlated to examples of affliction data as outputs. Affliction training data may be received from database. In an embodiment, affliction training data may be iteratively updated as a function of the input and output results of past iterations of affliction machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

Continuing to refer to FIG. 1, processor 104 may be configured to generate at least one affliction datum using an affliction machine-learning model. As used in the current disclosure, a "affliction machine-learning model" is a machine-learning model that is configured to generate affliction data based time series data 108 and/or associated time series labels 116. Affliction machine-learning model may be consistent with any machine-learning model described herein and below in FIG. 2. Inputs to the affliction machine-learning model may include time series data 108, ECG data, time series label data, and the like. Outputs from the affliction machine-learning model may include affliction data tailored to the time series data 108 and/or time series labels 116. Affliction training data may include a plurality of data entries containing a plurality of inputs that are correlated to a plurality of outputs for training a processor by a machine-learning process. In an embodiment, affliction training data may include a plurality of time series data and time series labels as inputs correlated to examples of affliction data as outputs. Affliction training data may be received from database. In an embodiment, affliction training data may be iteratively updated as a function of the input and output results of past iterations of affliction machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With further reference to FIG. 1, processor 104 may determining the at least one recommendation datum 124 using a lookup table. A "lookup table," for the purposes of this disclosure, is a data structure, such as without limitation an array of data, that maps input values to output values. A lookup table may be used to replace a runtime computation with an indexing operation or the like, such as an array indexing operation. A look-up table may be configured to pre-calculate and store data in static program storage, calculated as part of a program's initialization phase or even stored in hardware in application-specific platforms. Data within the lookup table may include previous examples of recommendation data 124 compared to time series data 108, time series label data, and/or any other data associated with a user. Data within the lookup table may be received from database 400. Lookup tables may also be used to identify recommendation data 124 by matching an input value to an output value by matching the input against a list of valid (or invalid) items in an array. In a non-limiting example, a lookup table may look up the user's time series data and/or time series labels as inputs and output recommendation data 124 indicating that user should follow up with a stress test. Processor 104 may be configured to "lookup" or input one or more times series data 108, time series labels 116, demographic data, and the like. Output of the lookup table may comprise recommendation data 124. Data from the lookup table may be compared to examples of recommendation data 124, for instance, and without limitation using string comparisons, numerical comparisons such as subtraction operations, or the like.

Still referring to FIG. 1, additionally, or alternatively, determining the at least one recommendation datum 124 may include generating a recommendation score for each recommendation datum 124. A "recommendation score," for the purpose of this disclosure, is a quantified measure that represents need for recommendation data. In an embodiment, recommendation score may include a ranking out of five stars, out of a scale of 1-10, a percentage score, and the like. Alternatively, or additionally, recommendation score may be an alphabetic score, such as, but not limited to, "A+", "A", "A−", "B+", "B", "B−", C+", "C", "C−", D+", "D", "D−", "F", and the like. In some cases, recommendation score may be manually scored by medical professionals described herein. In other cases, recommendation score may be generated, by processor 104, through one or more scoring algorithm or model such as, without limitation, machine learning models described herein, that takes into account various data such as time series data 108, electronic health record data associated with a patient, lifestyle factors, and other relevant health metrics. In a non-limiting example, a higher recommendation score may indicate a greater need for associated recommendation data. For example, a recommendation score of "84" associated with a stress test may indicate a greater need for patients to follow up with a stress test. In a further exemplary embodiment, a recommendation score of "54" associated with an echocardiogram may indicate that a need for an echocardiogram is less than the need for a stress test for patient. Alternatively, or additionally, a fuzzy inferencing system for determination of recommendation score may be employed, where any or all recommendation scores may be represented as values and/or fuzzy sets for linguistic variables measuring the same. An inferencing system may use one or more fuzzy inferencing rules, as described below in FIG. 6, to output one or more linguistic variable values and/or defuzzified values indicating recommendation scores.

With continued reference to FIG. 1, processor 104 may generate a recommendation confidence score as a function of the generation of the recommendation datum as a function of the recommendation machine learning model. As used in the current disclosure, a "recommendation confidence score" is quantitative measurement of the accuracy of the generation of the recommendation datum 124. Accuracy of the assignment of the recommendation datum 124 may refer to likelihood of an accurate generation of recommendation for the patient. Processor 104 may generate a recommendation confidence score for each recommendation datum 124. Processor 104 may calculate a recommendation confidence score based on the similarity or dissimilarity between the recommendation data generated based on time series data. Various similarity metrics can be employed, such as Euclidean distance, cosine similarity, Jaccard similarity, or any other appropriate measure for the type of data being compared. Processor 104 may use the calculated similarity or dissimilarity values to generate a recommendation confidence score. This score may represent the level of confidence or certainty in the accuracy in the generation of recommendation datum 124. The score can be computed based on statistical methods, probability models, or decision rules based on time series data and/or time series label 116. A recommendation confidence score may be used to normalize one or more generated recommendation data onto a comparable scale. Normalization techniques can include min-max scaling, z-score normalization, or logarithmic transformation. In an embodiment, if the generation of recommendation datum 124 is likely to be accurate then the recommendation confidence score may be high, conversely generation of recommendation datum 124 is likely inaccurate then the recommendation confidence score may be low. A confidence score may be expressed as a numerical score, a linguistic value, alphanumeric score, or an alphabetical score. Recommendation confidence score may be represented as a score used to reflect the level of accuracy of the generation of recommendation datum 124. A non-limiting example, of a numerical score, may include a scale from 1-10, 1-100, 1-1000, and the like, wherein a rating of 1 may represent an inaccurate recommendation datum, whereas a rating of 10 may represent an accurate recommendation datum. In another non-limiting example, linguistic values may include, "Highly Accurate," "Moderately Accurate," "Moderately Inaccurate," "Highly Inaccurate," and the like. In some embodiments, linguistic values may correspond to a numerical score range. For example, recommendation datum that receives a score between 50-75, on a scale from 1-100, may be considered "Moderately Accurate."

Still referring to FIG. 1, processor 104 may be configured to compare each recommendation score to a threshold recommendation score. As used in the current disclosure, a "threshold recommendation score" is a predefined level of need by the patient for a recommendation datum. In an exemplary embodiment, threshold recommendation score may be any calculated or predetermined value. Threshold recommendation score may serve as a cutoff point or boundary beyond which generated recommendation datum may be relevant to a patient. In an embodiment, when the recommendation score surpasses the threshold affliction score, recommendation datum is accepted as accurate and relevant. Conversely, if the recommendation score falls below this threshold, the prediction may be deemed less relevant, and further review and manual intervention may be warranted.

For example, threshold affliction score may be "75" to limit affliction datum to include suspected conditions and/or suspected diseases with substantial likelihood for patient.

Continuing to refer to FIG. 1, additionally, or alternatively, generating a recommendation score may include generating an affliction score. An "affliction score," for the purpose of this disclosure, is a quantified measure that represents an evaluation of the likelihood of the presence of a suspected condition or a suspected disease a patient is suspected to be experiencing. In an embodiment, affliction score may include a ranking out of five stars, out of a scale of 1-10, a percentage score, and the like. Alternatively, or additionally, affliction score may be an alphabetic score, such as, but not limited to, "A+", "A", "A−", "B+", "B", "B−", C+", "C", "C−", D+", "D", "D−", "F", and the like. In some cases, affliction score may be manually scored by medical professionals described herein. In other cases, affliction score may be generated, by processor 104, through one or more scoring algorithm or model such as, without limitation, machine learning models described herein, that takes into account various data such as time series data 108, time series labels 116, electronic health record data associated with a patient, lifestyle factors, and other relevant health metrics. In a non-limiting example, a higher affliction score may indicate a greater probability of a presence of a suspected affliction. For example, an affliction score of "90" associated with Coronary Artery Disease may indicate a high likelihood Coronary Artery Disease is present in a patient. In a further exemplary embodiment, a recommendation score of "48" associated with heart failure may indicate a patient is less likely to be experiencing heart failure than a likelihood Coronary Artery Disease is present in the patient. Alternatively, or additionally, a fuzzy inferencing system for determination of affliction score may be employed, where any or all affliction scores may be represented as values and/or fuzzy sets for linguistic variables measuring the same. An inferencing system may use one or more fuzzy inferencing rules, as described below in FIG. 6, to output one or more linguistic variable values and/or defuzzified values indicating affliction scores.

Still referring to FIG. 1, processor 104 may be configured to compare each affliction score to a threshold affliction score. As used in the current disclosure, a "threshold affliction score" is a predefined level of probability that a patient is suffering from a suspected condition and/or suspected disease. In an exemplary embodiment, threshold affliction score may be any calculated or predetermined value. Threshold affliction score may serve as a cutoff point or boundary beyond which generated affliction datum may be relevant to a patient. In an embodiment, when the affliction score surpasses the threshold affliction score, affliction datum is accepted as accurate and relevant. Conversely, if the affliction score falls below this threshold, the prediction may be deemed less relevant, and further review and manual intervention may be warranted. For example, threshold affliction score may be "70" to limit affliction datum to include suspected conditions and/or suspected diseases with substantial likelihood for patient.

With continued reference to FIG. 1, processor 104 may be configured to generate a time series model 132 as a function of the time series data 108. As used in the current disclosure, "time series model" is a visual representation of information that conveys aspects of the time series data. Time series model may refer to any type of data that is presented visually through graphical representations, such as charts, graphs, diagrams, maps, and other visual aids. These visual representations may represent complex data and are used to communicate information in a way that is easier to comprehend. Time series model 132 can come in many forms, depending on the type of data being presented and the intended audience. For example, a line graph may be used to show the trend of a particular data set over time, while a pie chart may be used to display the distribution of different categories within a larger data set. Other types of time series model 132 may include bar charts, scatter plots, heat maps, network diagrams, and the like. Time series model 132 may include a graphical representation of one or more elements of time series data 108 and/or time series labels 116. In some embodiments, time series model 132 may include plotting time series data 108 and/or time series labels 116 along a continuum. As used in the current disclosure, a "continuum" is a spectrum or a range of values, qualities, or attributes that exist along a single dimension or scale. A continuum may represent a continuous progression from one extreme to another, without any clear-cut boundaries or discrete categories. In a continuum, there are no distinct breakpoints or divisions, instead, there is a gradual transition or progression from one end to the other. In some embodiments, a continuum may represent qualitative traits that exist on a spectrum. In a non-limiting example, a continuum may represent one or more characteristics associated with time series data 108 and/or time series labels 116. Graphical data may include a plurality of continuums, wherein each continuum represents one more trait or characteristic of the representations. In some embodiments, multiple continuums may be combined to generate an XY plot or an XYZ plot. Processor 104 may be configured to add labels to the axes, a title, legends, and any other visual elements that provide context to graphical data. Processor 104 may additionally be configured to customize the appearance of data points, lines, or other graphical elements. In order to plot the graphical data processor 104 may be configured to organize time series data 108 and/or time series labels 116 in a suitable format. In a non-limiting example, this may involve having two sets of values: the independent variable (x-values) representing the continuum or range, and the dependent variable (y-values) representing the corresponding aspects of time series data 108 and/or time series labels 116. Processor 104 may identify and implement a plotting library to generate time series model 132. Examples of plotting libraries may include but are not limited to Matplotlib for Python, ggplot for R, or Plotly for JavaScript. Processor 104 may then pass the x and y values to the plotting library's function dedicated to creating line plots. This will generate a plot with the data points representing various aspects of time series data 108 and/or time series labels 116 along the continuum.

With continued reference to FIG. 1, processor 104 may be configured to create a user interface data structure. As used in this disclosure, "user interface data structure" is a data structure representing a specialized formatting of data on a computer configured such that the information can be effectively presented for a user interface. User interface data structure may include the plurality of components. In some cases user interface data structure may further include time series label 116, time series model 132, and the like. In some cases, user interface data structure further includes any data as described in this disclosure. Processor 104 may be configured to generate user interface data structure using any combination of data as described in this disclosure.

With continued reference to FIG. 1, processor 104 may further be configured to transmit the user interface data structure. Transmitting may include, and without limitation, transmitting using a wired or wireless connection, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. Processor 104 may transmit the data described above to a database wherein the data may be accessed from a database, processor 104 may further transmit the data above to a device display or another computing device, such as display device 136 described below.

Still referring to FIG. 1, processor 104 may be configured to display time series model 132 using a display device 136. As used in the current disclosure, a "display device" is a device that is used to display content. A display device 136 may include a user interface 140. A "user interface," as used herein, is a means by which a user and a computer system interact; for example, through the use of input devices and software. In some cases, time series model and/or other data described herein such as, without limitation, time series data 108, time series labels 116, and/or the like may also be displayed through display device 136 using user interface 140. A user interface may include a graphical user interface (GUI), command line interface (CLI), menu-driven user interface, touch user interface, voice user interface (VUI), form-based user interface, any combination thereof, and the like. A user interface may include a smartphone, smart tablet, desktop, or laptop operated by the user. In an embodiment, the user interface may include a graphical user interface. A "graphical user interface (GUI)," as used herein, is a graphical form of user interface that allows users to interact with electronic devices. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull down menu. When any option is clicked in this menu, then the pull down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface may be directly influenced using graphical control elements such as widgets. A "widget," as used herein, is a user control element that allows a user to control and change the appearance of elements in the user interface. In this context a widget may refer to a generic GUI element such as a check box, button, or scroll bar to an instance of that element, or to a customized collection of such elements used for a specific function or application (such as a dialog box for users to customize their computer screen appearances). User interface controls may include software components that a user interacts with through direct manipulation to read or edit information displayed through user interface. Widgets may be used to display lists of related items, navigate the system using links, tabs, and manipulate data using check boxes, radio boxes, and the like.

With further reference to FIG. 1, in an embodiment, user interface 140 may include one or more graphical locator and/or cursor facilities allowing a user to interact with time series data 108, time series label 116, and/or any other data, or even processes described herein; for instance, and without limitation, by using a touchscreen, touchpad, mouse, keyboard, and/or other manual data entry device, user may enter user input containing selecting specific regions, adding comments, adjusting parameter, and/or the like. In an embodiment, user may be a medical professional. As used in this disclosure, "medical professional" is an individual who has undergone education, training, and licensing in the field of medicine, with the primary responsibility of providing medical care to patients. For example, medical professional may be a physician, cardiologist, nurse, physician assistants, and the like. Additionally, or alternatively, user input may include a user selection of at least one portion of time series data and a user annotation for each portion of the at least one portion of time series data. As used in this disclosure, "annotation" is an informative label, metadata, and the like that is added to any data by a medical processional as described herein.

Still referring to FIG. 1, processor 104 is configured to overlay the at least one recommendation datum 124 onto the time series model 132. As used in this disclosure, "overlay" is superimposing additional information onto a visual representation of a physical or digital model. In an exemplary embodiment, time series label 116, recommendation datum 124, affliction datum, recommendation score, affliction score, or any other data described herein may be overlaid and visualized onto the time series model 132. Additionally, or alternatively, each of time series label 116, recommendation datum 124, affliction datum, recommendation score, and affliction score may be overlaid on a portion of time series model 132 associated with a portion of time series data 108 used for time series label 116, recommendation datum 124, affliction datum, recommendation score, affliction score, and the like. For example, processor 104 may be configured to highlight a portion of time series model 132 by drawing a circle around relevant portion of time series model and any of superimpose recommendation datum 124, affliction datum, recommendation score, and affliction score for that relevant portion of time series model 132.

Figure 2:
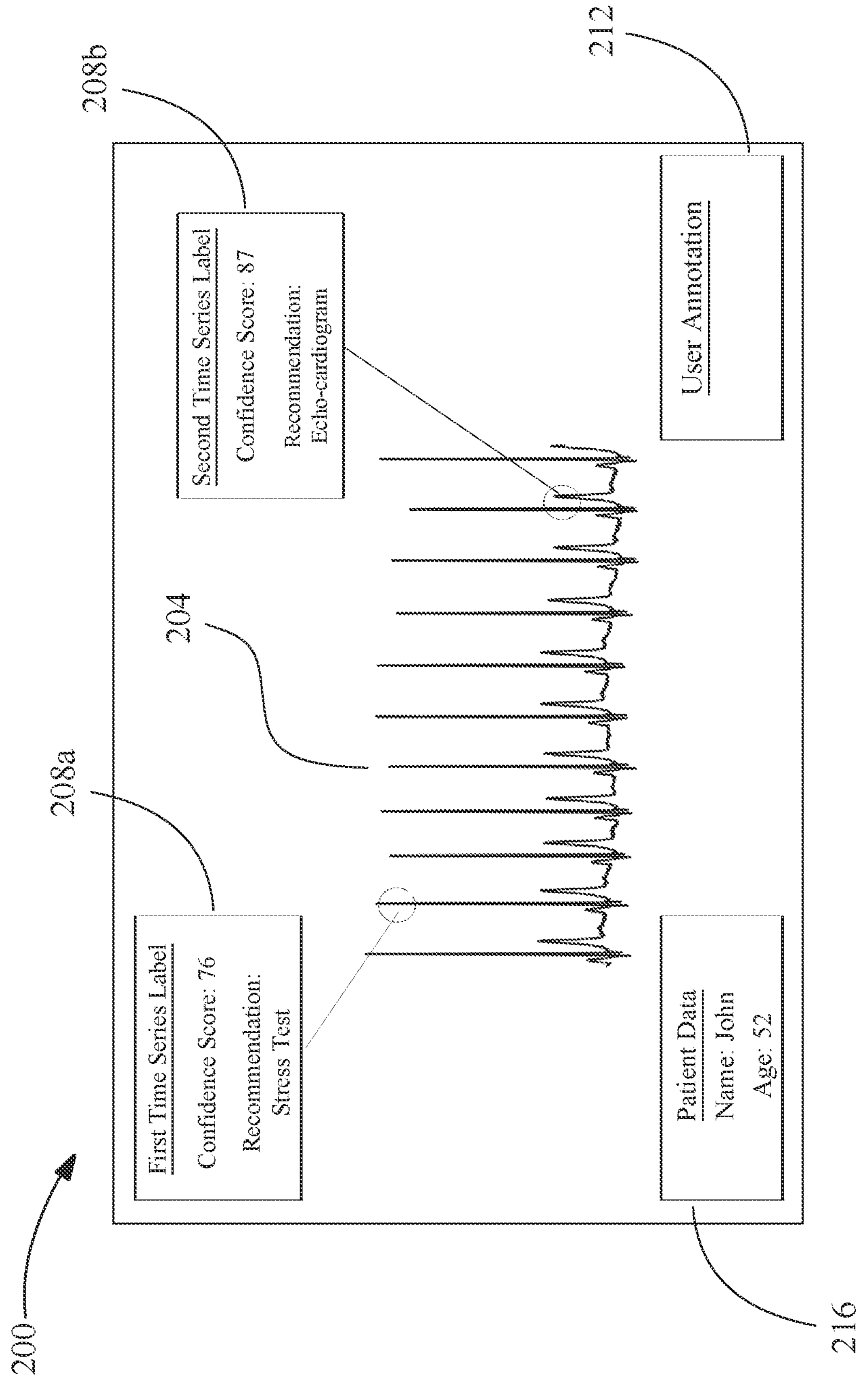
FIG. 2 is an exemplary embodiment of a time series model.

Referring now to FIG. 2, an exemplary embodiment 200 of a time series model as described in this disclosure is illustrated. As shown in FIG. 2, exemplary embodiment 200 of time series model may include time series data 204. Time series data 204 may be consistent with any time series data. Additionally, or alternatively, exemplary embodiment 200 of time series model may include a first time series label 208*a* and a second time series label 208*b*. First time series label 208*a* and a second time series label 208*b* may be consistent with any time series label described herein. In one embodiment, first time series label 208*a* and second time series label may be generated using a first label machine learning model and a second machine learning model of a label machine learning model described herein. Additionally, or alternatively, exemplary embodiment 200 of time series model may include a first time series label 208*a* and a second time series label 208*b* generated by one machine learning model of label machine learning model. Additionally, or alternatively, exemplary embodiment 200 of time series model may include user annotation 212. User annotation 212 may be any user annotation described herein. Additionally, or alternatively, exemplary embodiment 200 of time series model may include patient data 216. Patient data may be any patient data described herein.

Figure 3:
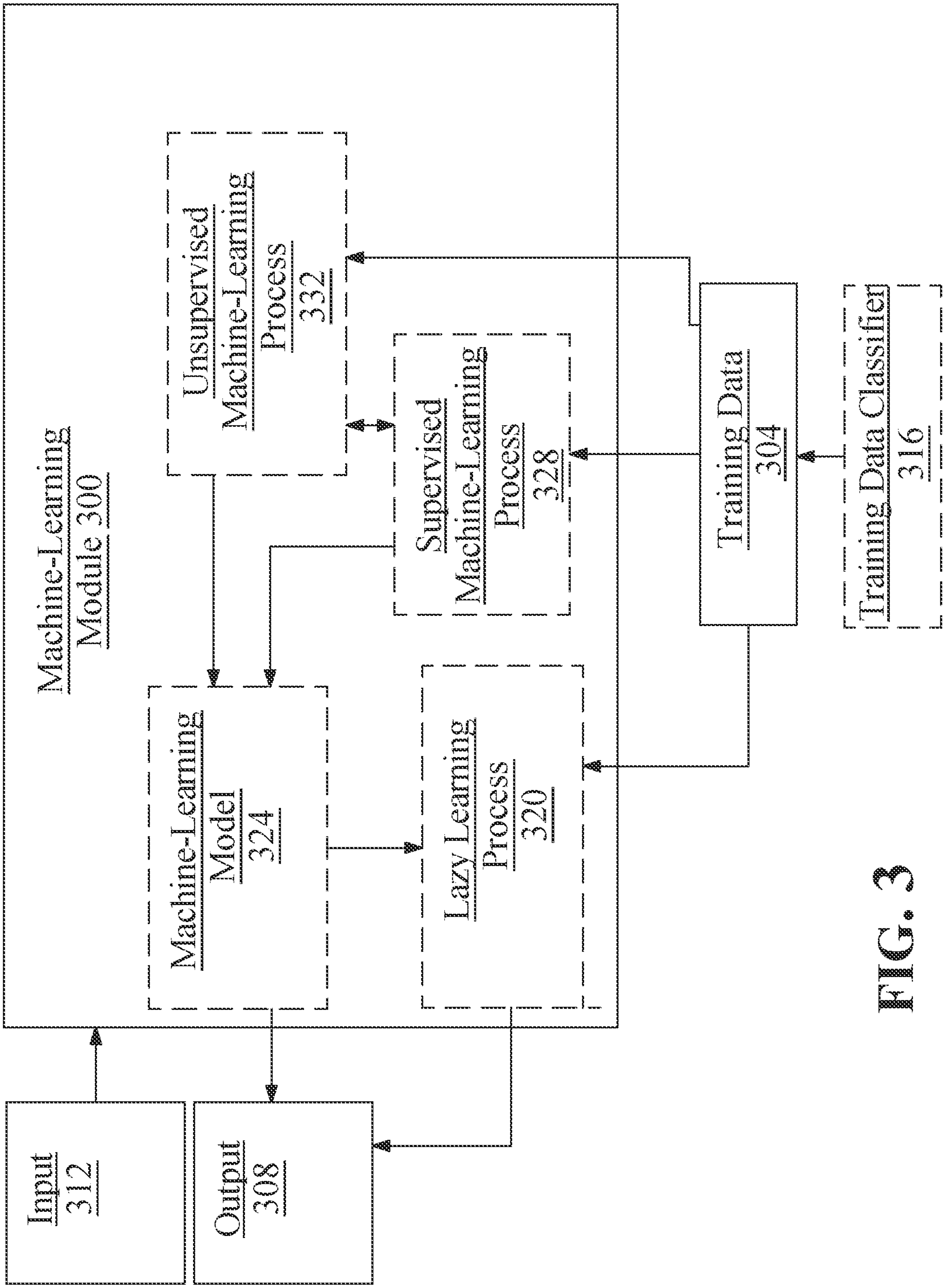
FIG. 3 is a block diagram of an exemplary machine-learning process.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify time series data 108 correlated to examples of a plurality of time series labels 124.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 3, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may identify as having poor quality data, where "poor quality" is defined as having a signal to noise ratio below a threshold value.

As a non-limiting example, and with further reference to FIG. 3, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 3, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units In some embodiments, and with continued reference to FIG. 3, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a data structure representing and/or instantiating a mathematical and/or algorithmic representation of a relationship between inputs and outputs, as generated using any machine-learning process including without limitation any process as described above and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include time series data 108 as described above as inputs, plurality of time series labels 116 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

With further reference to FIG. 3, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 3, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 3, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 3, one or more processes or algorithms described above may be performed by at least a dedicated hardware unit 332. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 332 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 332 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 332 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 4:
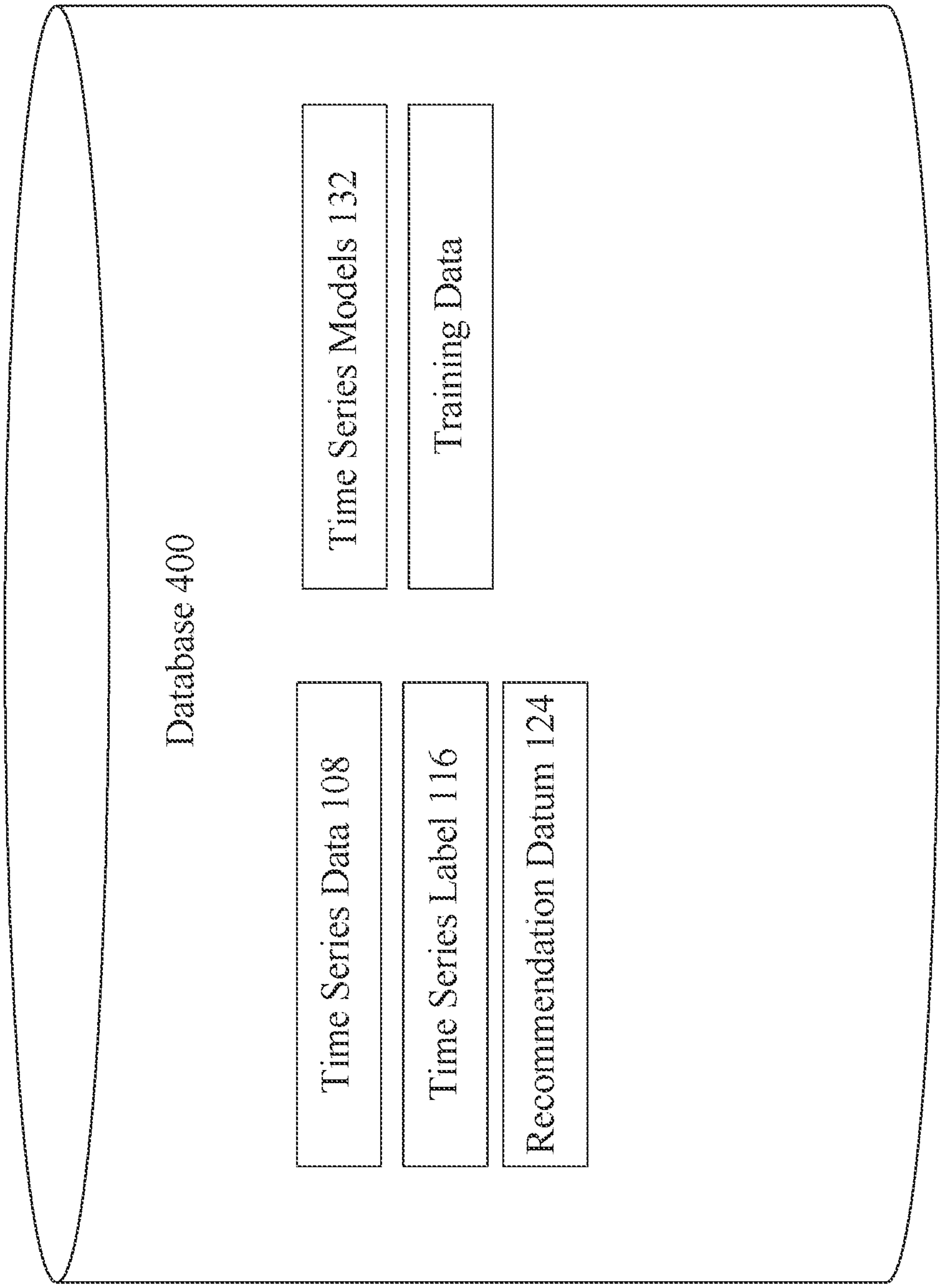
FIG. 4 is a block diagram of an exemplary embodiment of a database.

Now referring to FIG. 4, an exemplary database 400 is illustrated by way of block diagram. In an embodiment, any past or present versions of any data disclosed herein may be stored within the database 400 including but not limited to: time series data 108, time series label 116, training data, recommendation datum 124, affliction datum, time series models 132, and the like. Processor 104 may be communicatively connected with database 400. For example, in some cases, database 400 may be local to processor 104. Alternatively or additionally, in some cases, database 400 may be remote to processor 104 and communicative with processor 104 by way of one or more networks. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connects directly, dynamically, and non-hierarchically to as many other computing devices as possible. A "network topology" as used in this disclosure is an arrangement of elements of a communication network. Database 400 may be implemented, without limitation, as a relational database, a key-value retrieval database such as a NOSQL database, or any other format or structure for use as a database that a person skilled in the art would recognize as suitable upon review of the entirety of this disclosure. Database 400 may alternatively or additionally be implemented using a distributed data storage protocol and/or data structure, such as a distributed hash table or the like. Database 400 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Figure 5:
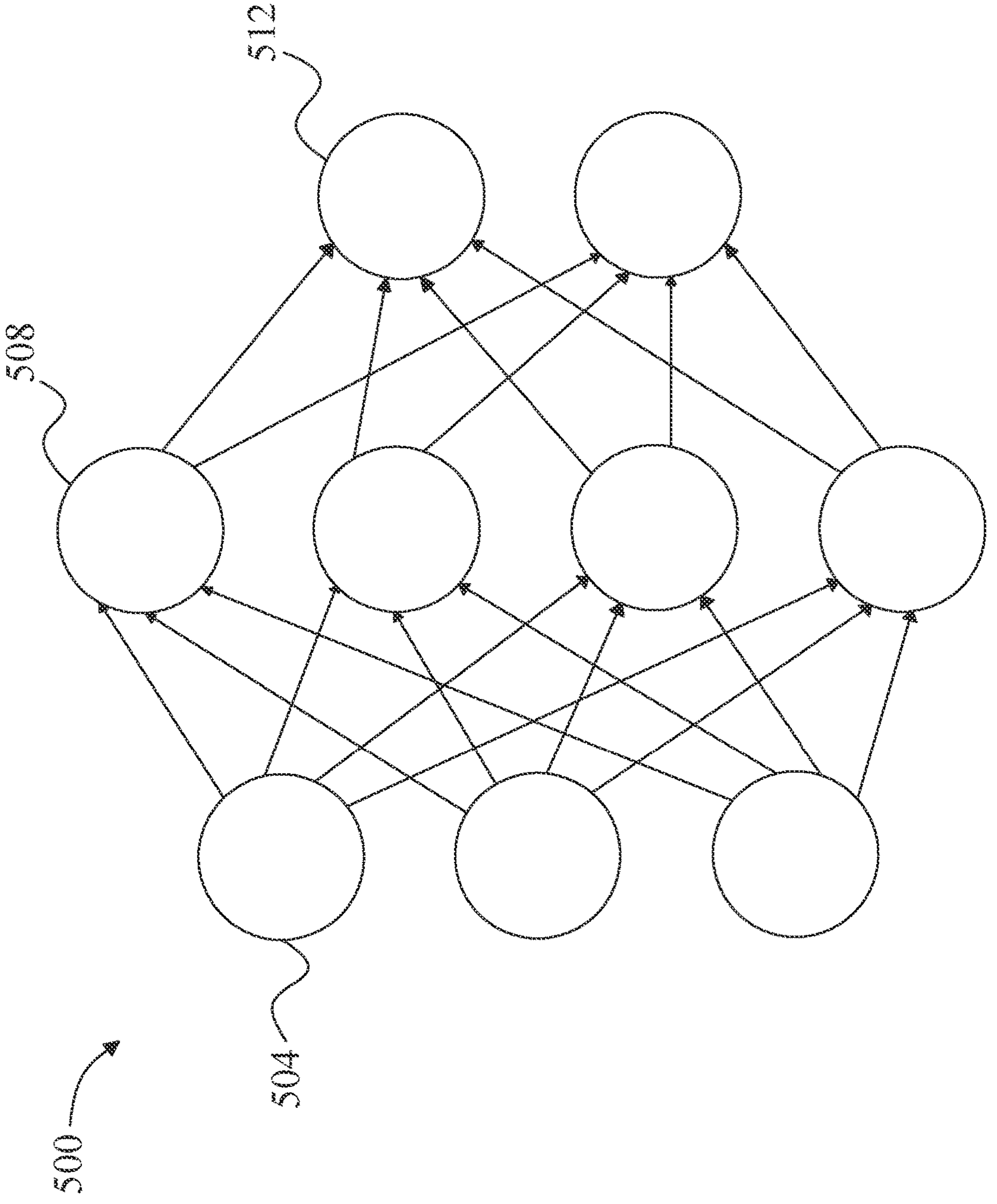
FIG. 5 is a diagram of an exemplary embodiment of a neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
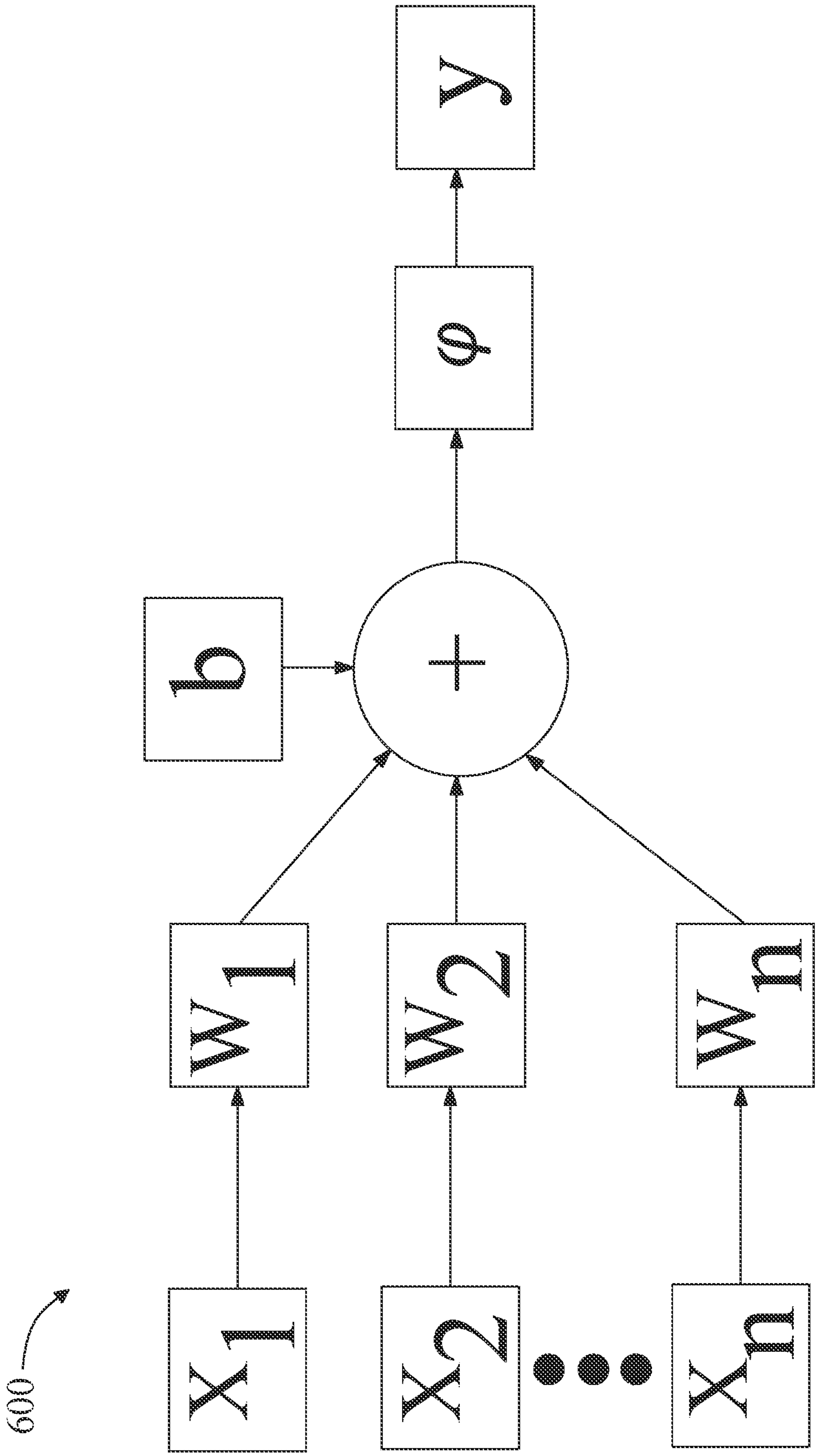
FIG. 6 is a diagram of an exemplary embodiment of a node of a neural network.

Referring now to FIG. 6, an exemplary embodiment of a node 600 of a neural network is illustrated. A node may include, without limitation a plurality of inputs x, that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tan h (hyperbolic tangent) function, of the form $$\frac{e^x - e^{-x}}{e^x + e^{-x}},$$

a tan h derivative function such as $f(x)=\tan h^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda\begin{cases} \alpha(e^x - 1) & \text{for } x < 0 \\ x & \text{for } x \geq 0 \end{cases}.$$

Fundamentally, there is no limit to the nature of functions of inputs x, that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 7:
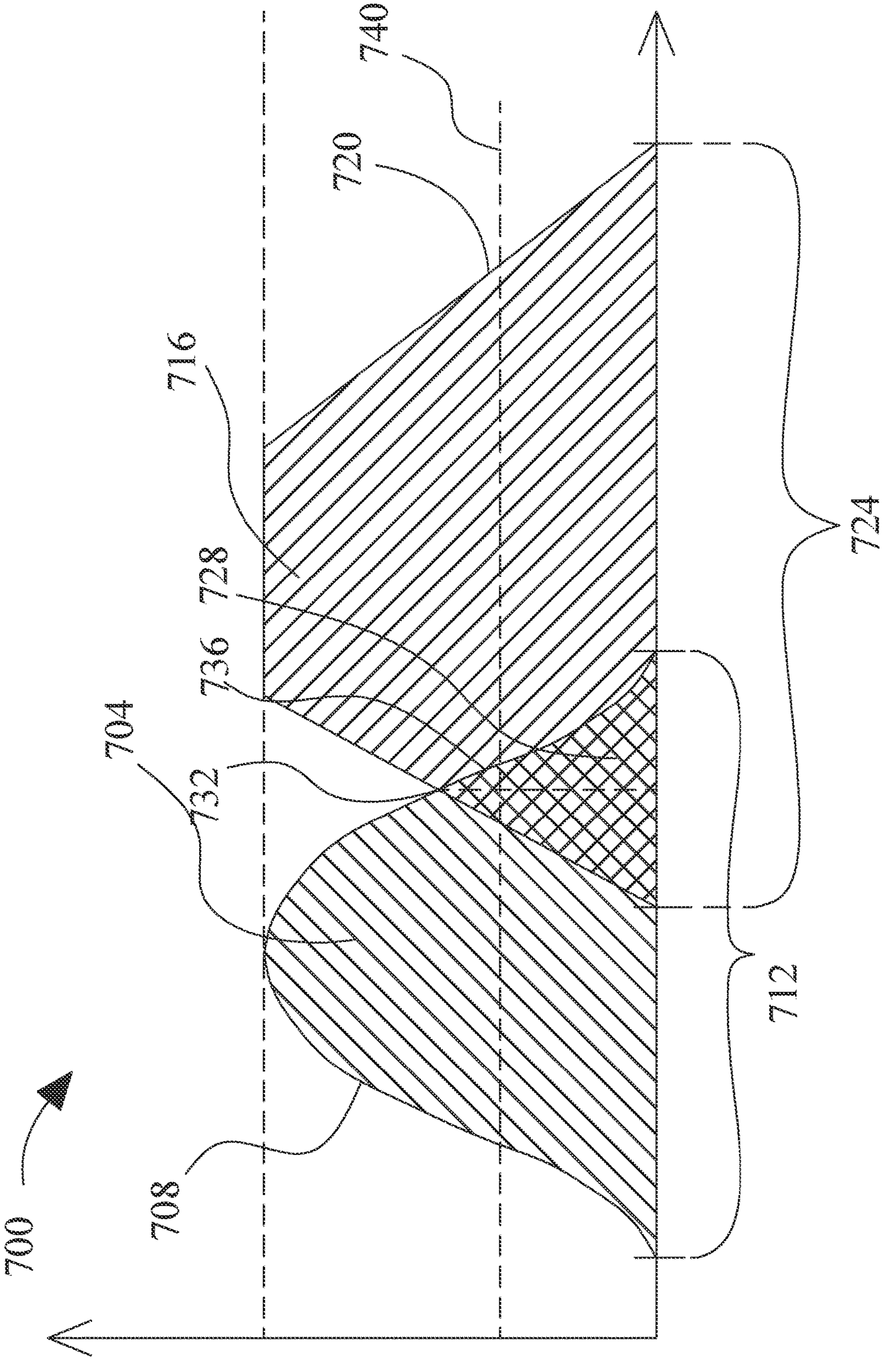
FIG. 7 is an illustration of an exemplary embodiment of fuzzy set comparison.

Referring now to FIG. 7, an exemplary embodiment of fuzzy set comparison 700 is illustrated. A first fuzzy set 704 may be represented, without limitation, according to a first membership function 708 representing a probability that an input falling on a first range of values 712 is a member of the first fuzzy set 704, where the first membership function 708 has values on a range of probabilities such as without limitation the interval [0,1], and an area beneath the first membership function 708 may represent a set of values within first fuzzy set 704. Although first range of values 712 is illustrated for clarity in this exemplary depiction as a range on a single number line or axis, first range of values 712 may be defined on two or more dimensions, representing, for instance, a Cartesian product between a plurality of ranges, curves, axes, spaces, dimensions, or the like. First membership function 708 may include any suitable function mapping first range 712 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, & \text{for } x > c \text{ and } x < a \\ \frac{x-a}{b-a}, & \text{for } a \leq x < b \\ \frac{c-x}{c-b}, & \text{if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 7, first fuzzy set 704 may represent any value or combination of values as described above, including output from one or more machine-learning models. A second fuzzy set 716, which may represent any value which may be represented by first fuzzy set 704, may be defined by a second membership function 720 on a second range 724; second range 724 may be identical and/or overlap with first range 712 and/or may be combined with first range via Cartesian product or the like to generate a mapping permitting evaluation overlap of first fuzzy set 704 and second fuzzy set 716. Where first fuzzy set 704 and second fuzzy set 616 have a region 728 that overlaps, first membership function 708 and second membership function 720 may intersect at a point 732 representing a probability, as defined on probability interval, of a match between first fuzzy set 704 and second fuzzy set 716. Alternatively, or additionally, a single value of first and/or second fuzzy set may be located at a locus 736 on first range 712 and/or second range 724, where a probability of membership may be taken by evaluation of first membership function 708 and/or second membership function 720 at that range point. A probability at 728 and/or 732 may be compared to a threshold 740 to determine whether a positive match is indicated. Threshold 740 may, in a non-limiting example, represent a degree of match between first fuzzy set 704 and second fuzzy set 716, and/or single values therein with each other or with either set, which is sufficient for purposes of the matching process; for instance, threshold may indicate a sufficient degree of overlap between an output from one or more machine-learning models. Alternatively, or additionally, each threshold may be tuned by a machine-learning and/or statistical process, for instance and without limitation as described in further detail below.

Figure 8:
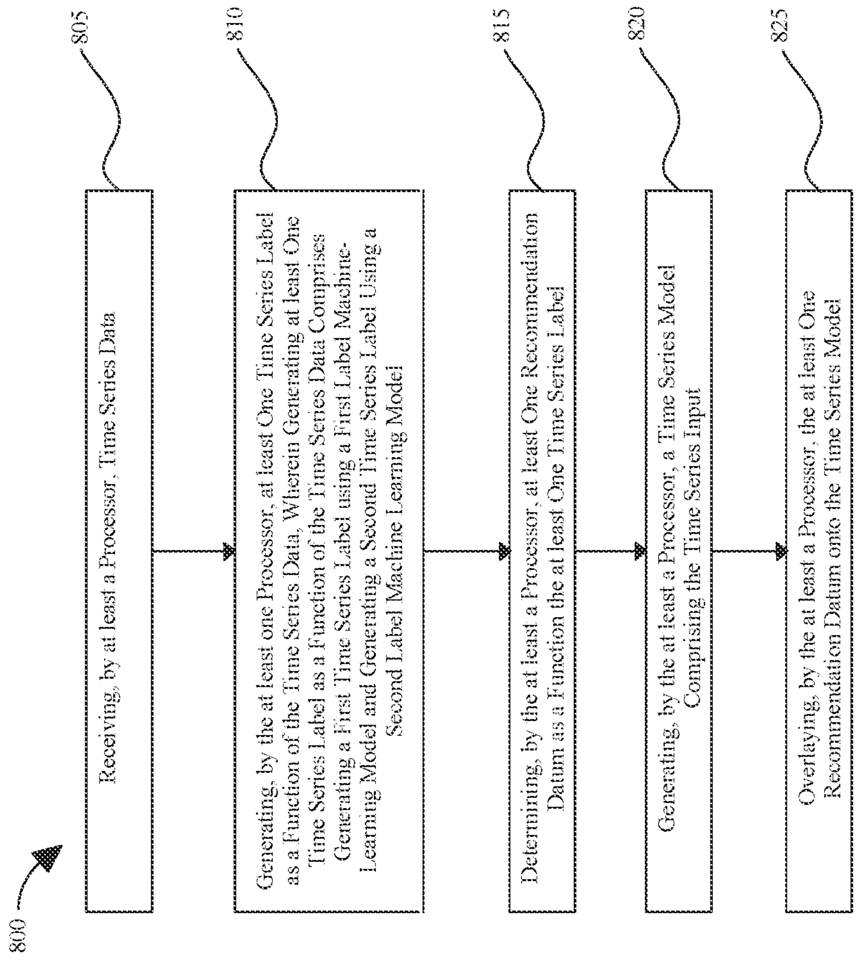
FIG. 8 is a flow diagram of an exemplary method for synthesizing time series data and diagnostic data.
Figure 9:
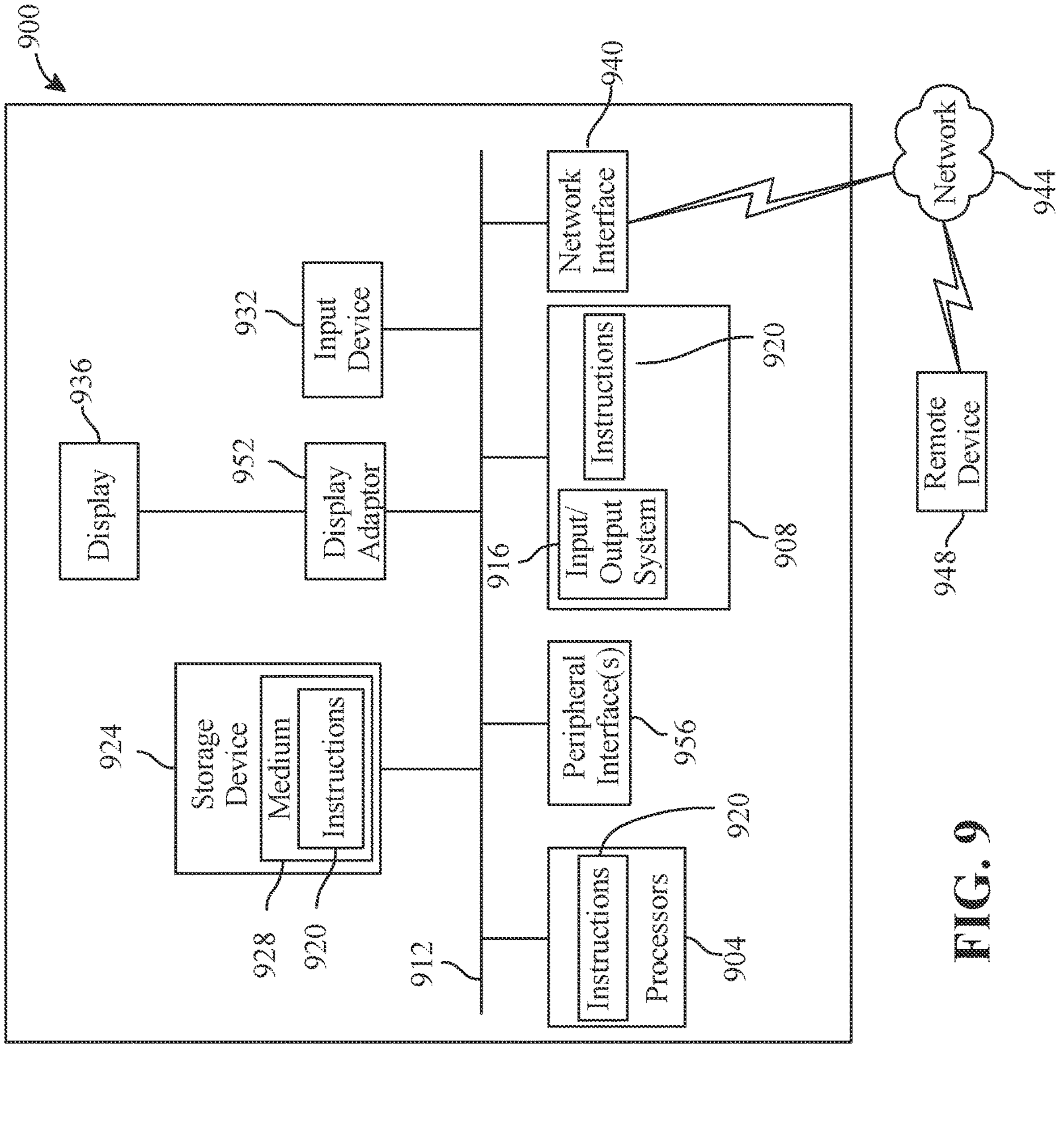
FIG. 9 is a block diagram of a computing system that can be used to implement any one or more of the methodologies disclosed herein and any one or more portions thereof.

Referring now to FIG. 8, a flow diagram of an exemplary method 800 for synthesizing time series data and diagnostic data is illustrated. At step 805, method 800 includes receiving, by at least a processor, time series data. In an embodiment, the time series data may comprise electrocardiogram (ECG) data. These may be implemented as described and with reference to FIGS. 1-7.

Still referring to FIG. 8, at step 810, method 800 includes generating, by the at least one processor, at least one time series label as a function of the time series data. Generating the at least one time series label as a function of the time series data comprises generating a first time series label using a first label machine-learning model and generating a second time series label using a second label machine learning model. In an embodiment, generating the at least one time series label as a function of the time series data may comprise training, by the at least a processor, a label machine leaning model as a function of label training data and generating, by the at least a processor, the at least one time series label as a function of the trained label machine learning model. These may be implemented as described and with reference to FIGS. 1-7.

Still referring to FIG. 8, at step 815, method 800 includes determining, by the at least a processor, at least one recommendation datum as a function the at least one time series label. In an embodiment, determining the at least one recommendation datum as a function the at least one time series label may comprise training, by the at least a processor, a recommendation machine leaning model as a function of recommendation training data and determining, by the at least a processor, the at least one recommendation datum as a function of the trained recommendation machine learning model. Additionally, or alternatively, determining the at least one recommendation datum as a function the at least one time series label may comprise generating, by the at least a processor, a recommendation score for each recommendation datum of the at least one recommendation datum. Further, additionally, or alternatively, each recommendation datum of the at least one recommendation datum may comprise an affliction datum. Additionally, or alternatively, determining the at least one recommendation datum as a function the at least one time series label may comprise training, by the at least a processor, an affliction machine leaning model as a function of affliction training data and generating, by the at least a processor, the at least one affliction datum as a function of the trained affliction machine learning model. Furthermore, additionally, or alternatively, determining the at least one recommendation datum as a function the at least one time series label may comprise generating, by the at least a processor, an affliction score for each affliction datum of the at least one affliction datum. These may be implemented as described and with reference to FIGS. 1-7.

Still referring to FIG. 8, at step 820, method 800 includes generating, by the at least a processor, a time series model comprising the time series input. This may be implemented as described and with reference to FIGS. 1-7.

Still referring to FIG. 8, at step 825, method 800 includes overlaying, by the at least a processor, the at least one recommendation datum onto the time series model. In an embodiment, overlaying the at least one recommendation datum onto the time series model may comprise overlaying, by the at least a processor, a confidence score for the at least one recommendation. In an embodiment, overlaying the at least one recommendation datum onto the time series model may comprise overlaying a first recommendation datum relating to a first time series label and overlaying a second recommendation datum relating to a second time series label. These may be implemented as described and with reference to FIGS. 1-7.

Still referring to FIG. 8, method 800 may include receiving, by the at least a processor, a user input comprising at least one annotation for the time series data. Additionally, overlaying the at least one recommendation datum onto the time series model may include overlaying, by the at least a processor, the at least one annotation onto the time series model. These may be implemented as described and with reference to FIGS. 1-7.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

FIG. 8 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and apparatuses according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for synthesizing time series data and diagnostic data, wherein the apparatus comprises:

at least a processor; and a memory communicatively connected to the at least a processor, wherein the memory containing instructions configuring the at least a processor to:

receive, from a sensor, time series data including electrocardiogram (ECG) data;

generate at least one time series label as a function of the time series data, wherein the at least one time series label indicates an anomaly, and generating at least one time series label as a function of the time series data comprises:

extracting a plurality of features from the time series data, wherein the plurality of features are constrained by a lexicon related to a field of medicine;

generating a first time series label using a first label machine-learning model that has been trained with first machine-learning model training data comprising an input of nodes comprising time series data, one or more intermediate layers of nodes, and an output layer of nodes comprising at least one time series label, wherein generating the first time series label comprises:

selecting a set of training examples from the first machine-learning model training data according to one or more cohorts relevant to a classification task, wherein the set of training examples is selected to represent a range of values in proportions matching a distribution of the plurality of features according to relative frequency, such that at least a portion of the plurality of features encountered more frequently in a population of the time-series data is represented by the set of training examples than a portion of the plurality of values encountered less frequently;

retraining the first label machine-learning model using the selected set of training examples; and generating the first time series label using the retrained first label machine-learning model; and generating a second time series label using a second label machine learning model, wherein training a second label machine learning model comprises using second machine learning training data comprising the time series label output from the first label machine-learning model correlated to a second time series label output;

generate a first confidence score for the first time series label;

generate a second confidence score for the second time series label;

normalize the first time series label based on the first confidence score;

normalize the second time series label based on the second confidence score;

determine, using a recommendation machine-learning model, at least one recommendation datum for each of the first and second time series labels;

generate a time series model comprising the ECG data;

overlay the at least one recommendation datum onto the time series model, wherein overlaying the at least one recommendation datum onto the time series model comprises superimposing information onto a visual representation of a physical model; and circle, using the at least a processor, a portion of the time series model as a function of the anomaly.

2. The apparatus of claim 1, wherein determining the at least one recommendation datum comprises:

training the recommendation machine leaning model as a function of recommendation training data; and determining the at least one recommendation datum as a function of the trained recommendation machine learning model.

3. The apparatus of claim 1, wherein determining the at least one recommendation datum comprises generating a recommendation score for each recommendation datum of the at least one recommendation datum.

4. The apparatus of claim 1, wherein each recommendation datum of the at least one recommendation datum comprises at least one affliction datum.

5. The apparatus of claim 4, wherein determining the at least one recommendation datum comprises:

training an affliction machine leaning model as a function of affliction training data; and generating the at least one affliction datum as a function of the trained affliction machine learning model.

6. The apparatus of claim 1, wherein the processor is further configured to:

receive a user input comprising at least one annotation for the time series data.

7. The apparatus of claim 6, wherein overlaying the at least one recommendation datum onto the time series model comprises overlaying, by the at least a processor, the at least one annotation onto the time series model.

8. The apparatus of claim 1, wherein overlaying the at least one recommendation datum onto the time series model comprises overlaying, by the at least a processor, a confidence score for the at least one recommendation.

9. The apparatus of claim 1, wherein overlaying the at least one recommendation datum onto the time series model comprises overlaying a first recommendation datum relating to the first time series label and overlaying a second recommendation datum relating to the second time series label.

10. A method for generating annotations for electronic records, the method comprising:

receiving, by at least a processor, time series data including electrocardiogram (ECG) data;

generating, by the at least a processor, at least one time series label as a function of the time series data, wherein the at least one time series label indicates an anomaly, generating at least one time series label as a function of the time series data comprises:

extracting a plurality of features from the time series data, wherein the plurality of features are constrained by a lexicon related to a field of medicine;

generating a first time series label using a first label machine-learning model that has been trained with first machine-learning model training data comprising an input of nodes comprising time series data, one or more intermediate layers of nodes, and an output layer of nodes comprising at least one time series label, wherein generating the first time series label comprises:

selecting a set of training examples from the first machine-learning model training data according to one or more cohorts relevant to a classification task, wherein the set of training examples is selected to represent a range of values in proportions matching a distribution of the plurality of features according to relative frequency, such that at least a portion of the plurality of features encountered more frequently in a population of the time-series data is represented by the set of training examples than a portion of the plurality of values encountered less frequently;

retraining the first label machine-learning model using the selected set of training examples; and generating the first time series label using the retrained first label machine-learning model; and generating a second time series label using a second label machine learning model, wherein training a second label machine learning model comprises using second machine learning training data comprising the time series label output from the first label machine learning model correlated to a second time series label output;

generate a first confidence score for the first time series label;

generate a second confidence score for the second time series label;

normalize the first time series label based on the first confidence score;

normalize the second time series label based on the second confidence score;

determining, by the at least a processor, at least one recommendation datum as a function the first and second time series labels;

generating, by the at least a processor, a time series model comprising the ECG data;

overlaying, by the at least a processor, the at least one recommendation datum onto the time series model, wherein overlaying the at least one recommendation datum onto the time series model comprises superimposing information onto a visual representation of a physical model; and circling, using the at least a processor, a portion of the time series model as a function of the anomaly.

11. The method of claim 10, wherein determining the at least one recommendation datum comprises:

training, by the at least a processor, the recommendation machine leaning model as a function of recommendation training data; and determining, by the at least a processor, the at least one recommendation datum as a function of the trained recommendation machine learning model.

12. The method of claim 10, wherein determining the at least one recommendation datum comprises generating, by the at least a processor, a recommendation score for each recommendation datum of the at least one recommendation datum.

13. The method of claim 10, wherein each recommendation datum of the at least one recommendation datum comprises an affliction datum.

14. The method of claim 13, wherein determining the at least one recommendation datum comprises:

training, by the at least a processor, an affliction machine leaning model as a function of affliction training data; and generating, by the at least a processor, the at least one affliction datum as a function of the trained affliction machine learning model.

15. The method of claim 10, further comprising receiving, by the at least a processor, a user input comprising at least one annotation for the time series data.

16. The method of claim 10, wherein overlaying the at least one recommendation datum onto the time series model comprises overlaying, by the at least a processor, the at least one annotation onto the time series model.

17. The method of claim 10, wherein overlaying the at least one recommendation datum onto the time series model comprises overlaying, by the at least a processor, a confidence score for the at least one recommendation.

18. The method of claim 10, wherein overlaying the at least one recommendation datum onto the time series model comprises overlaying a first recommendation datum relating to the first time series label and overlaying a second recommendation datum relating to the second time series label.

* * * * *